US007932026B2

(12) United States Patent
Seshagiri

(10) Patent No.: US 7,932,026 B2
(45) Date of Patent: Apr. 26, 2011

(54) EGFR MUTATIONS

(75) Inventor: Somasekar Seshagiri, San Carlos, CA (US)

(73) Assignee: Genentech, Inc., South San Francisco, CA (US)

( * ) Notice: Subject to any disclaimer, the term of this patent is extended or adjusted under 35 U.S.C. 154(b) by 34 days.

(21) Appl. No.: 11/145,566

(22) Filed: Jun. 2, 2005

(65) Prior Publication Data

US 2005/0272083 A1    Dec. 8, 2005

Related U.S. Application Data

(60) Provisional application No. 60/666,068, filed on Mar. 28, 2005, provisional application No. 60/635,344, filed on Dec. 10, 2004, provisional application No. 60/577,425, filed on Jun. 4, 2004.

(51) Int. Cl.
C12Q 1/68 (2006.01)
C12P 19/34 (2006.01)
C12M 1/34 (2006.01)
G01N 33/48 (2006.01)

(52) U.S. Cl. .......... 435/6; 435/91.2; 435/287.1; 436/63; 436/64

(58) Field of Classification Search .................. None
See application file for complete search history.

(56) References Cited

U.S. PATENT DOCUMENTS

| 4,683,195 | A | 7/1987 | Mullis et al. ............ 435/6 |
| 4,683,203 | A | 7/1987 | Anton et al. ........... 435/94 |
| 5,679,683 | A | 10/1997 | Bridges et al. ........ 514/267 |
| 5,869,245 | A | 2/1999 | Yeung ................... 435/6 |
| 2002/0102685 | A1* | 8/2002 | Sibilia et al. .......... 435/184 |
| 2006/0147959 | A1 | 7/2006 | Bell et al. |
| 2009/0202989 | A1 | 8/2009 | Hillan |

FOREIGN PATENT DOCUMENTS

| EP | 0332435 | 9/1989 |
| WO | WO 2004/111273 | 12/2004 |
| WO | 2005/118876 | 12/2005 |

OTHER PUBLICATIONS

Fuijimoto 2005 Cancer Research vol. 65 p. 11478.*
Kawesha et al. International Journal of Cancer 2000 vol. 89 p. 469.*
Mukohara et al. Jurnal of the national cancer institue 2005 vol. 97 p. 1185.*
Thomas et al. 2004 Cancer Treatment Reviews vol. 30 p. 255.*
Suzuki et al. 2003 Lung Cancer vol. 42 p. 35.*
Barbacid et al. 1987 Annual Review Biochem. vol. 56 p. 779.*
Pao et al. (PLOS Medicine Mar. 2005 vol. 2 p. e73) teaches.*
Downward et al. (Nature Reviews Cancer Jan. 2003 vol. 3 p. 11).*
Moroni et al. (The lancet May 2005 vol. 6 p. 279).*
Cariello, Resolution of a Missense Mutant in Human Genomic DNA by Denaturing Gradient Fel Electrophoresis and Direct Sequencing Using in Vitro SNA Amplification: HPRT$_{Munich}$, The American Society of Human Genetics, vol. 42, p. 726, 1988.
Cotton et al., "Reactivity of Cytosine and Thymine in Single-Base-Pair Mismatches with Hydroxylamine and Osmium Tetroxide and its Application to the Study of Mutations", Proc. Natl. Acad. Sci. USA, vol. 85, 4397, 1988.
Del Tito et al, "Automated Fluorescent Analysis Procedure for Enzymatic Mutation Detection", Clinical Chemistry 44:731-739, 1998.
Dvir, et al., "The Inhibition of EGF-dependent Proliferation of Keratinocytes by Tyrphostin Tyrosine Kinase Blockers", J Cell Biol., 113:857-865 (1991).
Gullick, "Prevalend of Aberrant Expression of the Epidermal Growth Factor Receptor in Human Cancers", British Medical Bulletin 1991, 47:87-98.
Han e al., "Predictive and Prognostic Impact of Epidermal Growth Factor Receptor Mutation in Non-Small Cell Lung Cancer Patients Treated with Gefitinib", Journal od Clinical Onocology, vol. 23, No. 11, p. 2493-2501, 2005.
Lei et al., "Enhancement of Chemosensitivity and Programmed Cell Death by Tyrosine Kinase Inhibitors Correlates with EGFR Expression in Non-Small Cell Lung Cancer Cells", Anticancer Research 1999; 10 19:221-8.
Lynch et.al., "Activating Mutations in the epidermal Growth Factor Receptor Underlying Responsiveness of Non-Small-Cell Lung Cancer to Gefitinib", New England Journal of Medicine, vol. 350 No. 21 p. 2129-2139 (2004).
Meyers et al., "Detection of Single Base Substitutions by Ribonuclease Cleavage at Mismataches in RNA:DNA Duplexes", Science, vol. 230, p. 1242, 1985.
Modijtahedi and Dean, "The Receptor for RGF and its Ligands: Expression, Prognostic Value and Target for Therapy in Cancer", International Journal of Oncology 1994, 4:277-96.
Newton et al., "Analysis of any Point Mutation in DNA. The Amplification Refractory Mutation System (ARMS)", Nucleic Acids Research, vol. 17, p. 2503-2507, 1989.
Novack et al., "Detection of Single Base-Pair Mismatches in DNA by Chemical Modification followed by Electrophoresis in 15% Polyacrylamide Gel", Proc. Natl. Acad. Sci. USA, vol. 83, p. 586, 1986.
Orita et al., "Rapid and Sensitive Detection of Point Mutations and DNA Polymorphisms Using the Polymerase Chain Reaction", Genomics, vol. 5, pp. 874-879, 1989.
Orita et al., "Detection of Polymorphisms of Human DNA by Gel Electrophoresis as Single-Strand Conformation Polymorphisms", Proc. Natl. Acad. Sci. USA vol. 86, pp. 2766-2770, 1989.
Paez et al., "EGFR Mutations in Lung Cancer: Correlation with Clinical Response to Gefitinib Therapy", Science, vol. 304, p. 1497-1500, 2004.
Panek, et al., "In Vitro Pharmacological Characterization of PD 166285, a New Nanomolar Potent and Broadly Active Protein Tyrosine Kinase Inhibitor", Journal of Pharmacology and Experimental Therapeutics 283, 1433-1444 (1997).

(Continued)

Primary Examiner — Katherine Salmon
(74) Attorney, Agent, or Firm — Jones Day

(57) ABSTRACT

The present invention relates to mutations in Epidermal Growth Factor Receptor (EGFR) and methods of detecting such mutations as well as prognostic methods method for identifying a tumors that are susceptible to anticancer therapy such as chemotherapy and/or kinase inhibitor treatment. The methods involve determining the presence of a mutated EGFR gene or mutated EGFR protein in a tumor sample whereby the presence of a mutated EGFR gene or protein indicates the tumor is susceptible to treatment.

24 Claims, 12 Drawing Sheets

OTHER PUBLICATIONS

Pao et al., "EGF Receptor Gene Mutations are Common in Lung Cancers from "Never Smokers" and are Associated with Sensitivity of Tumors to Gefitinib and Erlotinib", The Procedding of the National Academy of Sciences of the USA, vol. 101, No. 36, p. 13306-13311, 2004.

Posner et al., "Kinetic Model of the Epidermal Growth Factor (EGF) Receptor Tyrosine Kinase and a Possible Mechanism of its Activation by EGF*" J. Biol. Chem. 267 (29):20638-47 (1992).

Ruano and Kidd, "Direct Haplotyping of Chromosomal Segments from Multiple Heterozygotes Via Allele-Specific PCR Amplification", Nucleic Acids Research, vol. 17, p. 8392, 1989.

Saiki et al., "Primer-Directed Enzymatic Amplification of DNA with a Thermostable DNA Polymerase", Science 239:487, 1988.

Salomon et al., "Epidermal Growth Factor-Related Peptides and Their Receptors in Human Malignancies", Critical Reviews in Oncology/Hematology 1995;19:183-232.

Schaefer et al. "A Discrete Three-Amino Acid Segment (LVI) at the C-terminal End of Kinase-impaired ErbB3 is required for Transactivation of ErbB2*", 1999 J. Biol. Chem. 274, 859-866.

Shenk et al., "Biochemical Method for Mapping Mutational Alterations in DNA with S1 Nuclease: The Location of Deletions and Temperature-Sensitive Mutations in Simian Virus 40*", Proc. Natl. Acad. Sci. USA, vol. 72, p. 989, 1975.

Veale et al., "The Relationship of Quantitative Epidermal Growth Factor Receptor Expression in Non-Small Cell Lung Cancer to Long Term Survival", Br J Cancer 1993;68:162-5.

Winter et al., A Method to Detect and Characterize Point Mutations in Transcribed Genes: Amplification and Overexpression of the Mutant c-Ki-ras Allele in Human Tumor Cells:, Proc. Natl. Acad. Sci. USA, vol. 82, p. 7575, 1985.

Wu et al., "The Ligation Amplification Reaction (LAR)-Amplification of Specific DNA Sequences Using Sequential Rounds of Template-Dependent Ligation", Genomics, vol. 4, pp. 560-569 (1989).

Ahrendt. S.A., et al., "Molecular Detection of Tumor Cells in Bronchoalveolar Lavage fluid from Patients with Early Stage Lung Cancer", Journal of the National Cancer Institute. vol. 91, No. 4, pp. 332-339, (1999).

Lynch, T.J., et al., "Activating Mutations in the epidermal Growth Factor Receptor Underlying Responsiveness of Non-Small-Cell Lung Cancer to Gefitinb". The New England Journal of Medicine, vol. 350. No. 21, pp. 2129-2139, (2004).

Miller, V.A., et al., "Pilot Trial of the Epidermal Growth Factor Receptor Tyrosine Kinase Inhibitor Gefainib Plus Carboplatin and Paclitaxel in Patients with Stage HIB or IV Non-Small-Cell Lung Cancer", Journal of Clinical Oncology, vol. 21, No. 11, pp. 2094-2100, (2003).

Raponi et al., "KRAS mutations predict response to EGFR inhibitors," 2008. Current Opinion in Pharmacology 8:413-418.

Van Cutsem et al., "KRAS status and efficacy in the first-line treatment of patients with metastatic colorectal cancer (mCRC) treated with FOLFIRI with or without cetuximab: The CRYSATAL experience," 2008 ASCO Annual Meeting, Abstract No. 2.

Frykman et al., "K-ras, Cancer, EGFR Inhibitors and the FDA: Precedent-Setting ODAC Expected Mid-December" The Washington Pharma Bulletin, published Oct. 7, 2008, by the Stanford Group Company.

Amado et al., "Wild-type KRAS is required for panitumumab efficacy in patients with metastatic colorectal cancer." 2008, J Clin Oncol 26(10): 1626-1634.

Tuma, "KRAS Mutation Status PredictsResponsiveness to Panitumumab," Oncology Times, Nov. 25, 2007. p. 34.

Miller et al., "Molecular characteristics of bronchioloalvcelar carcinoma and adenocarcinoma, bronchioloalveolar carcinoma subtype, predict response to erlotinib" 2008, J Clin Oncol 26 (9): 1472-1478.

Lee et al., "Impact of Epidemial Growth Factor Receptor (EGFR) Kinase Mutations, EGFR Gene Amplifications, and KRAS Mutations on Survival of Pancreatic Adenocarcinoma," 2007, Cancer 109: 1561-1569.

Chen, "KRAS mutation analysis in patients (pts) with locally advanced pancreatic cancer (LAPC) treated with getitinib and chemoradiation therapy (CT-RT) in a phase 1 trial," 2000 ASCO Annual Meeting. Abstract: No. 4106.

Van Zandwijk et al., "EGFR and KRAS mutation as criteria for treatment with tyrosine kinase inhibitors: retro-and prospective observations in non-small-cell lung cancer," 2007. Annals of Oncology 18:99-103.

Pao et al., "KRAS Mutations and Primary Resistance of Lung Adenocarcinomas to Gefitinib or Erlotinib," 2005, PLOS Medicine 2: 57-61.

Eberhard et al., "Correlation of mutations in EGFR with clinical outcomes m NSCLC patients treated with erlotinib," 2004, European Journal of Cancer Supplements, Proceedings of the 16th EORTC-NCI-AACR Symposium on Molecular Targets and Cancer Therapeutics, vol. 2. No. 8.

Moroni et al., "KRAS mutations and primary resistance of lung adenocarcinomass to getfinib or erlotinib." 2005, PLOS Medicine 2(1):1549-1676.

Amler et al., "Predicting clinical benefit in non-small-cell lung cancer patients with epidermal growth factor tyrosine kinase inhibitors," 2005, Cold Spring Harbor Symposia on Quantitative Biology, 70:483-488.

Eberhard et al., "Mutations in the epidermal growth factor receptor and in KRAS are predictive and prognostic indicators in patients with non-small-cell lung cancer treated with chemotherapy alone or in combination with erlotinib," 2005, Journal of Clinical Oncology, 23(25):5900-5909.

Eberhard et al., "Mutations in EGFR, HER2, KRAS, and BRAF in NSCLC: Prevalences and correlations with clinical outcomes in patients treated with carboplatin and paclitaxel with or without erlotinib," 2005, Lung Caner, 49:S62.

Reck et al., "Molecular markers such as EGFR and KRAS mutations as predictors of sensitivity to erlotinib in patients with NSCLC: exploratory subanalyses of TALENT, a phase III trial," 2005, Lung Cancer, 49:S112.

Lievre et al., "KRAS mutation status is predictive of response to cetuximab therapy in colorectal cancer," 2006, Cancer Research, 66(8):3992-3995.

Ogino et al., "Molecular alterations in tumors and response to combination chemotherapy with getitinib for advanced colorectal cancer," 2005. Clinical Cancer Research, 11(18):6650-6656.

Moroni et al., 2008, "EGFR Fish in colorectal cancer: what is the current reality?" Lancet Oncology 9:402-403.

Difiore et al., 2007, "Clinical relevance of KRAS mutation detection in metastatic colorectal cancer treated by Cetuximab plus chemotherapy," British Journal of Cancer 96:1166-1169.

http://www.fda.gov/AboutFDA/CentersOffices/CDER/ucm172905. htm, last updated Jan. 11, 2010, downloaded Feb. 15, 2010.

LABEL for Erbitux (Cetuximab), United States, Indications and Usage Jul. 2009.

LABEL for Vectibix (Panitumumab), United States, Indications and Usage Jul. 2009.

LABEL for Erbitux (Cetuximab), Europe Date of first authorisation Jun. 29, 2004.

LABEL for Vectibix (Panitumumab), Europe Date of first authorisation Dec. 3, 2007.

USPTO Non-Final Office Action dated Jan. 15, 2010 in U.S. Appl. No. 11/915,830.

Hirschborn et al., 2002, "A comprehensive review of genetic association studies," Genetics in Medicine 4:45-61.

Cunningham et al., 2004, "Cetuximab monotherapy and Cetuximab plus Ironotecan-refractory metastatic colorectal cancer," New England Journal of Medicine 351:337-345.

Scartozzi et al., 2004, "Epidermal growth factor receptor (EGFR) status in primary colorectal tumors does not correlate with EGFR expression in related metastatic sites: implications for treatment with EGFR targeted monoclonal antibodies," Journal of Clinical Oncology 22:4772-4778.

Bleeker et al., 2001, "Prognostic significance of K-ras and TP53 mutations in the role of adjuvant chemotherapy on survival in patients with Dukes C colon cancer," Diseases of the Colon and Rectum 44:358-363.

Prix et al., 2002, "Diagnostic biochip array for fast and sensitive detection of K-ras mutations in stool," Clinical Chemistry 48:428-435.

Samowitz et al., 2001, "Relationship of Ki-ras mutations in colon cancers to tumor location, stage, and survival: a population-based study," Cancer Epidemiology, Biomarkers and Prevention 11:1193-1197.

Nelson et al., 1999, "Implications and prognostic value of K-ras mutation for early-stage lung cancer in women," Journal of the National Cancer Institute 91:2032-2038.

Blencke et al., 2004, "Characterization of a conserved structural determinant controlling protein kinase sensitivity to selective inhibitors," Chemistry and Biology 11:691-701.

* cited by examiner

```
  1 MRPSGTAGAA LLALLAALCP ASRALEEKKV CQGTSNKLTQ LGTFEDHFLS
 51 LQRMFNNCEV VLGNLEITYV QRNYDLSFLK TIQEVAGYVL IALNTVERIP
101 LENLQIIRGN MYYENSYALA VLSNYDANKT GLKELPMRNL QEILHGAVRF
151 SNNPALCNVE SIQWRDIVSS DFLSNMSMDF QNHLGSCQKC DPSCPNGSCW
201 GAGEENCQKL TKIICAQQCS GRCRGKSPSD CCHNQCAAGC TGPRESDCLV
251 CRKFRDEATC KDTCPPLMLY NPTTYQMDVN PEGKYSFGAT CVKKCPRNYV
301 VTDHGSCVRA CGADSYEMEE DGVRKCKKCE GPCRKVCNGI GIGEFKDSLS
351 INATNIKHFK NCTSISGDLH ILPVAFRGDS FTHTPPLDPQ ELDILKTVKE
401 ITGFLLIQAW PENRTDLHAF ENLEIIRGRT KQHGQFSLAV VSLNITSLGL
451 RSLKEISDGD VIISGNKNLC YANTINWKKL FGTSGQKTKI ISNRGENSCK
501 ATGQVCHALC SPEGCWGPEP RDCVSCRNVS RGRECVDKCN LLEGEPREFV
551 ENSECIQCHP ECLPQAMNIT CTGRGPDNCI QCAHYIDGPH CVKTCPAGVM
601 GENNTLVWKY ADAGHVCHLC HPNCTYGCTG PGLEGCPTNG PKIPSIATGM
651 VGALLLLLVV ALGIGLFMRR RHIVRKRTLR RLLQERELVE PLTPSGEAPN
701 QALLRILKET EFKKIKVLGS GAFGTVYKGL WIPEGEKVKI PVAIKELREA
751 TSPKANKEIL DEAYVMASVD NPHVCRLLGI CLTSTVQLIT QLMPFGCLLD
801 YVREHKDNIG SQYLLNWCVQ IAKGMNYLED RRLVHRDLAA RNVLVKTPQH
851 VKITDFGLAK LLGAEEKEYH AEGGKVPIKW MALESILHRI YTHQSDVWSY
901 GVTVWELMTF GSKPYDGIPA SEISSILEKG ERLPQPPICT IDVYMIMVKC
951 WMIDADSRPK FRELIIEFSK MARDPQRYLV IQGDERMHLP SPTDSNFYRA
1001 LMDEEDMDDV VDADEYLIPQ QGFFSSPSTS RTPLLSSLSA TSNNSTVACI
1051 DRNGLQSCPI KEDSFLQRYS SDPTGALTED SIDDTFLPVP EYINQSVPKR
1101 PAGSVQNPVY HNQPLNPAPS RDPHYQDPHS TAVGNPEYLN TVQPTCVNST
1151 FDSPAHWAQK GSHQISLDNP DYQQDFFPKE AKPNGIFKGS TAENAEYLRV
1201 APQSSEFIGA
```

FIGURE 1

| | |
|---|---|
| CCCCGGCGCAGCGCGGCCGCAGCAGCCTCCGCCCCCGCACGGTGTGAGCGCCCGACGCG | 60 |
| GCCGAGGCGGCCGGAGTCCCGAGCTAGCCCCGGCGGCCGCCGCCGCCCAGACCGGACGAC | 120 |
| AGGCCACCTCGTCGGCGTCCGCCCGAGTCCCCGCCTCGCCGCCAACGCCACAACCACCGC | 180 |
| GCACGGCCCCCTGACTCCGTCCAGTATTGATCGGGAGAGCCGGAGCGAGCTCTTCGGGGA | 240 |
| GCAGCGATGCGACCCTCCGGGACGGCCGGGGCAGCGCTCCTGGCGCTGCTGGCTGCGCTC | 300 |
| TGCCCGGCGAGTCGGGCTCTGGAGGAAAAGAAAGTTTGCCAAGGCACGAGTAACAAGCTC | 360 |
| ACGCAGTTGGGCACTTTTGAAGATCATTTTCTCAGCCTCCAGAGGATGTTCAATAACTGT | 420 |
| GAGGTGGTCCTTGGGAATTTGGAAATTACCTATGTGCAGAGGAATTATGATCTTTCCTTC | 480 |
| TTAAAGACCATCCAGGAGGTGGCTGGTTATGTCCTCATTGCCCTCAACACAGTGGAGCGA | 540 |
| ATTCCTTTGGAAAACCTGCAGATCATCAGAGGAAATATGTACTACGAAAATTCCTATGCC | 600 |
| TTAGCAGTCTTATCTAACTATGATGCAAATAAAACCGGACTGAAGGAGCTGCCCATGAGA | 660 |
| AATTTACAGGAAATCCTGCATGGCGCCGTGCGGTTCAGCAACAACCCTGCCCTGTGCAAC | 720 |
| GTGGAGAGCATCCAGTGGCGGGACATAGTCAGCAGTGACTTTCTCAGCAACATGTCGATG | 780 |
| GACTTCCAGAACCACCTGGGCAGCTGCCAAAAGTGTGATCCAAGCTGTCCCAATGGGAGC | 840 |
| TGCTGGGGTGCAGGAGAGGAGAACTGCCAGAAACTGACCAAAATCATCTGTGCCCAGCAG | 900 |
| TGCTCCGGGCGCTGCCGTGGCAAGTCCCCCAGTGACTGCTGCCACAACCAGTGTGCTGCA | 960 |
| GGCTGCACAGGCCCCCGGGAGAGCGACTGCCTGGTCTGCCGCAAATTCCGAGACGAAGCC | 1020 |
| ACGTGCAAGGACACCTGCCCCCCACTCATGCTCTACAACCCCACCACGTACCAGATGGAT | 1080 |
| GTGAACCCCGAGGGCAAATACAGCTTTGGTGCCACCTGCGTGAAGAAGTGTCCCCGTAAT | 1140 |
| TATGTGGTGACAGATCACGGCTCGTGCGTCCGAGCCTGTGGGGCCGACAGCTATGAGATG | 1200 |
| GAGGAAGACGGCGTCCGCAAGTGTAAGAAGTGCGAAGGGCCTTGCCGCAAAGTGTGTAAC | 1260 |
| GGAATAGGTATTGGTGAATTTAAAGACTCACTCTCCATAAATGCTACGAATATTAAACAC | 1320 |
| TTCAAAAACTGCACCTCCATCAGTGGCGATCTCCACATCCTGCCGGTGGCATTTAGGGGT | 1380 |

Figure 2a

| | |
|---|---|
| GACTCCTTCACACATACTCCTCCTCTGGATCCACAGGAACTGGATATTCTGAAAACCGTA | 1440 |
| AAGGAAATCACAGGGTTTTTGCTGATTCAGGCTTGGCCTGAAAACAGGACGGACCTCCAT | 1500 |
| GCCTTTGAGAACCTAGAAATCATACGCGGCAGGACCAAGCAACATGGTCAGTTTTCTCTT | 1560 |
| GCAGTCGTCAGCCTGAACATAACATCCTTGGGATTACGCTCCCTCAAGGAGATAAGTGAT | 1620 |
| GGAGATGTGATAATTTCAGGAAACAAAAATTTGTGCTATGCAAATACAATAAACTGGAAA | 1680 |
| AAACTGTTTGGGACCTCCGGTCAGAAAACCAAAATTATAAGCAACAGAGGTGAAAACAGC | 1740 |
| TGCAAGGCCACAGGCCAGGTCTGCCATGCCTTGTGCTCCCCGAGGGCTGCTGGGGCCCG | 1800 |
| GAGCCCAGGGACTGCGTCTCTTGCCGGAATGTCAGCCGAGGCAGGGAATGCGTGGACAAG | 1860 |
| TGCAACCTTCTGGAGGGTGAGCCAAGGGAGTTTGTGGAGAACTCTGAGTGCATACAGTGC | 1920 |
| CACCCAGAGTGCCTGCCTCAGGCCATGAACATCACCTGCACAGGACGGGGACCAGACAAC | 1980 |
| TGTATCCAGTGTGCCCACTACATTGACGGCCCCACTGCGTCAAGACCTGCCCGGCAGGA | 2040 |
| GTCATGGGAGAAAACAACACCCTGGTCTGGAAGTACGCAGACGCCGGCCATGTGTGCCAC | 2100 |
| CTGTGCCATCCAAACTGCACCTACGGATGCACTGGGCCAGGTCTTGAAGGCTGTCCAACG | 2160 |
| AATGGGCCTAAGATCCCGTCCATCGCCACTGGGATGGTGGGGCCCTCCTCTTGCTGCTG | 2220 |
| GTGGTGGCCCTGGGGATCGGCCTCTTCATGCGAAGGCGCCACATCGTTCGGAAGCGCACG | 2280 |
| CTGCGGAGGCTGCTGCAGGAGAGGGAGCTTGTGGAGCCTCTTACACCCAGTGGAGAAGCT | 2340 |
| CCCAACCAAGCTCTCTTGAGGATCTTGAAGGAAACTGAATTCAAAAAGATCAAAGTGCTG | 2400 |
| GGCTCCGGTGCGTTCGGCACGGTGTATAAGGGACTCTGGATCCCAGAAGGTGAGAAAGTT | 2460 |
| AAAATTCCCGTCGCTATCAAGGAATTAAGAGAAGCAACATCTCCGAAAGCCAACAAGGAA | 2520 |
| ATCCTCGATGAAGCCTACGTGATGGCCAGCGTGGACAACCCCCACGTGTGCCGCCTGCTG | 2580 |
| GGCATCTGCCTCACCTCCACCGTGCAGCTCATCACGCAGCTCATGCCCTTCGGCTGCCTC | 2640 |
| CTGGACTATGTCCGGGAACACAAAGACAATATTGGCTCCCAGTACCTGCTCAACTGGTGT | 2700 |

Figure 2b

```
GTGCAGATCGCAAAGGGCATGAACTACTTGGAGGACCGTCGCTTGGTGCACCGCGACCTG    2760

GCAGCCAGGAACGTACTGGTGAAAACACCGCAGCATGTCAAGATCACAGATTTTGGGCTG    2820

GCCAAACTGCTGGGTGCGGAAGAGAAAGAATACCATGCAGAAGGAGGCAAAGTGCCTATC    2880

AAGTGGATGGCATTGGAATCAATTTTACACAGAATCTATACCCACCAGAGTGATGTCTGG    2940

AGCTACGGGGTGACCGTTTGGGAGTTGATGACCTTTGGATCCAAGCCATATGACGGAATC    3000

CCTGCCAGCGAGATCTCCTCCATCCTGGAGAAAGGAGAACGCCTCCCTCAGCCACCCATA    3060

TGTACCATCGATGTCTACATGATCATGGTCAAGTGCTGGATGATAGACGCAGATAGTCGC    3120

CCAAAGTTCCGTGAGTTGATCATCGAATTCTCCAAAATGGCCCGAGACCCCCAGCGCTAC    3180

CTTGTCATTCAGGGGGATGAAAGAATGCATTTGCCAAGTCCTACAGACTCCAACTTCTAC    3240

CGTGCCCTGATGGATGAAGAAGACATGGACGACGTGGTGGATGCCGACGAGTACCTCATC    3300

CCACAGCAGGGCTTCTTCAGCAGCCCCTCCACGTCACGGACTCCCCTCCTGAGCTCTCTG    3360

AGTGCAACCAGCAACAATTCCACCGTGGCTTGCATTGATAGAAATGGGCTGCAAAGCTGT    3420

CCCATCAAGGAAGACAGCTTCTTGCAGCGATACAGCTCAGACCCCACAGGCGCCTTGACT    3480

GAGGACAGCATAGACGACACCTTCCTCCCAGTGCCTGAATACATAAACCAGTCCGTTCCC    3540

AAAAGGCCCGCTGGCTCTGTGCAGAATCCTGTCTATCACAATCAGCCTCTGAACCCCGCG    3600

CCCAGCAGAGACCCACACTACCAGGACCCCCACAGCACTGCAGTGGGCAACCCCGAGTAT    3660

CTCAACACTGTCCAGCCCACCTGTGTCAACAGCACATTCGACAGCCCTGCCCACTGGGCC    3720

CAGAAAGGCAGCCACCAAATTAGCCTGGACAACCCTGACTACCAGCAGGACTTCTTTCCC    3780

AAGGAAGCCAAGCCAAATGGCATCTTTAAGGGCTCCACAGCTGAAAATGCAGAATACCTA    3840

AGGGTCGCGCCACAAAGCAGTGAATTTATTGGAGCATGACCACGGAGGATAGTATGAGCC    3900

CTAAAAATCCAGACTCTTTCGATACCCAGGACCAAGCCACAGCAGGTCCTCCATCCCAAC    3960

AGCCATGCCCGCATTAGCTCTTAGACCCACAGACTGGTTTTGCAACGTTTACACCGACTA    4020

GCCAGGAAGTACTTCCACCTCGGGCACATTTTGGGAAGTTGCATTCCTTTGTCTTCAAAC    4080

TGTGAAGCATTTACAGAAACGCATCCAGCAAGAATATTGTCCCTTTGAGCAGAAATTTAT    4140
```

Figure 2c

| | |
|---|---|
| CTTTCAAAGAGGTATATTTGAAAAAAAAAAAAAGTATATGTGAGGATTTTTATTGATTGG | 4200 |
| GGATCTTGGAGTTTTTCATTGTCGCTATTGATTTTACTTCAATGGGCTCTTCCAACAAG | 4260 |
| GAAGAAGCTTGCTGGTAGCACTTGCTACCCTGAGTTCATCCAGGCCCAACTGTGAGCAAG | 4320 |
| GAGCACAAGCCACAAGTCTTCCAGAGGATGCTTGATTCCAGTGGTTCTGCTTCAAGGCTT | 4380 |
| CCACTGCAAAACACTAAAGATCCAAGAAGGCCTTCATGGCCCCAGCAGGCCGGATCGGTA | 4440 |
| CTGTATCAAGTCATGGCAGGTACAGTAGGATAAGCCACTCTGTCCCTTCCTGGGCAAAGA | 4500 |
| AGAAACGGAGGGGATGGAATTCTTCCTTAGACTTACTTTTGTAAAAATGTCCCCACGGTA | 4560 |
| CTTACTCCCCACTGATGGACCAGTGGTTTCCAGTCATGAGCGTTAGACTGACTTGTTTGT | 4620 |
| CTTCCATTCCATTGTTTTGAAACTCAGTATGCTGCCCCTGTCTTGCTGTCATGAAATCAG | 4680 |
| CAAGAGAGGATGACACATCAAATAATAACTCGGATTCCAGCCCACATTGGATTCATCAGC | 4740 |
| ATTTGGACCAATAGCCCACAGCTGAGAATGTGGAATACCTAAGGATAGCACCGCTTTTGT | 4800 |
| TCTCGCAAAAACGTATCTCCTAATTTGAGGCTCAGATGAAATGCATCAGGTCCTTTGGGG | 4860 |
| CATAGATCAGAAGACTACAAAAATGAAGCTGCTCTGAAATCTCCTTTAGCCATCACCCCA | 4920 |
| ACCCCCCAAAATTAGTTTGTGTTACTTATGGAAGATAGTTTTCTCCTTTTACTTCACTTC | 4980 |
| AAAAGCTTTTTACTCAAAGAGTATATGTTCCCTCCAGGTCAGCTGCCCCCAAACCCCCTC | 5040 |
| CTTACGCTTTGTCACACAAAAAGTGTCTCTGCCTTGAGTCATCTATTCAAGCACTTACAG | 5100 |
| CTCTGGCCACAACAGGGCATTTTACAGGTGCGAATGACAGTAGCATTATGAGTAGTGTGG | 5160 |
| AATTCAGGTAGTAAATATGAAACTAGGGTTTGAAATTGATAATGCTTTCACAACATTTGC | 5220 |
| AGATGTTTTAGAAGGAAAAAAGTTCCTTCCTAAAATAATTTCTACAATTGGAAGATTG | 5280 |
| GAAGATTCAGCTAGTTAGGAGCCCACCTTTTTTCCTAATCTGTGTGTGCCCTGTAACCTG | 5340 |
| ACTGGTTAACAGCAGTCCTTTGTAAACAGTGTTTTAAACTCTCCTAGTCAATATCCACCC | 5400 |
| CATCCAATTTATCAAGGAAGAAATGGTTCAGAAAATATTTTCAGCCTACAGTTATGTTCA | 5460 |
| GTCACACACACATACAAAATGTTCCTTTTGCTTTTAAAGTAATTTTTGACTCCCAGATCA | 5520 |
| GTCAGAGCCCCTACAGCATTGTTAAGAAAGTATTTGATTTTGTCTCAATGAAAATAAAA | 5580 |
| CTATATTCATTTCCACTCTAAAAAAAAAAAAAAAAAA | |

Figure 2d

EXON 18

| | | |
|---|---|---|
| EGFR protein | 716 | K V L G S G (SEQ ID NO: 3) |
| EGFR gene | 2392 | AAAGTGCTGGGCTCCGGT (SEQ ID NO: 4) |
| M1 (G719A) | | AAAGTGCTGTGCTCCGGT {KVL<u>A</u>SG} (SEQ ID NO: 5) (SEQ ID NO: 6) |
| M2 (G719C) | | AAAGTGCTGG<u>C</u>CTCCGGT {KVL<u>C</u>SG} (SEQ ID NO: 7) (SEQ ID NO: 8) |

EXON 19

| | | |
|---|---|---|
| EGFR protein | 743 | A I K E L R E A T S P K A N K E I L D (SEQ ID NO: 9) |
| EGFR gene | 2473 | GCTATCAAGGAATTAAGAGAAGCAACATCTCCGAAAGCCAACAAGGAAATCCTCGAT (SEQ ID NO: 10) |
| M3 (E746-A750del) | | GCTATCAA-------------------AACATCTCCGAAAGCCAACAAGGAAATCCTCGAT (SEQ ID NO: 11) |
| M4 (E748-R748del E749Q A750P) | | GCTATCAAG----------<u>C</u>AA<u>C</u>CAACATCTCCGAAAGCCAACAAGGAAATCCTCGAT (SEQ ID NO: 12) |
| M5 (L747S R748-P753del) | | GCTATCAAGGAAT-------------------CGAAAGCCAACAAGGAAATCCTCGAT (SEQ ID NO: 13) |
| M6 (S752-I759del) | | GCTATCAAGGAATTAAGAGAAGCAAC-----------------CCTCGAT (SEQ ID NO: 14) |
| M11 (A755V) | | GCTATCAAGGAATTAAGAGAAGCAACATCTCCGAAAG<u>T</u>CAACAAGGAAATCCTCGAT (SEQ ID NO: 15) |
| M12 (L747S) | | GCTATCAAGGAATTAAG<u>C</u>GAAGCAACATCTCCGAAAGCCAACAAGGAAATCCTCGAT (SEQ ID NO: 16) |
| M13 (E746K) | | GCTATCA<u>A</u>GAATTAAGAGAAGCAACATCTCCGAAAGCCAACAAGGAAATCCTCGAT (SEQ ID NO: 17) |

Figure 8

EXON 20

| | | |
|---|---|---|
| EGFR protein | 766 | M A S V D N P (SEQ ID NO: 18) |
| EGFR gene | 2542 | ATGGCC------AGCGTGGACAACCCC (SEQ ID NO: 19) |

M7 (M766-A767 AI ins)  ATGGCCATA---GCCAGCGTGGACAACCCC {MAIASVDNP}
(SEQ ID NO: 20)                                                    (SEQ ID NO: 21)

M8 (S768-V769 SVA ins) ATGGCCAGCGTGGCCAGCGTGGATAACCCC {MASVASVDNP}
(SEQ ID NO: 22)                                                    (SEQ ID NO: 23)

M9 (S768I)             ATGGCC------ATCGTGGACAACCCC    {MAIVDNP}
(SEQ ID NO: 24)                                                    (SEQ ID NO: 25)

EXON 21

| | | |
|---|---|---|
| EGFR protein | 856 | F G L A K L (SEQ ID NO: 26) |
| EGFR gene | 2812 | TTTGGGCTGGCCAAACTG (SEQ ID NO: 27) |

M10 (L858R) TTTGGGCGGGCCAAACTG {FGRAKL}
(SEQ ID NO: 28)                    (SEQ ID NO: 29)

M14 (L858P) TTTGGGCCGGCCAAACTG {FGPAKL}
(SEQ ID NO: 30)                    (SEQ ID NO: 31)

Figure 9

SEQUENCE LISTING

```
<160> NUMBER OF SEQ ID NOS: 60

<210> SEQ ID NO 1
<211> LENGTH: 1210
<212> TYPE: PRT
<213> ORGANISM: Homo sapiens

<400> SEQUENCE: 1

Met Arg Pro Ser Gly Thr Ala Gly Ala Ala Leu Leu Ala Leu Leu
  1               5                  10                  15

Ala Ala Leu Cys Pro Ala Ser Arg Ala Leu Glu Glu Lys Lys Val
                 20                  25                  30

Cys Gln Gly Thr Ser Asn Lys Leu Thr Gln Leu Gly Thr Phe Glu
                 35                  40                  45

Asp His Phe Leu Ser Leu Gln Arg Met Phe Asn Asn Cys Glu Val
                 50                  55                  60

Val Leu Gly Asn Leu Glu Ile Thr Tyr Val Gln Arg Asn Tyr Asp
                 65                  70                  75

Leu Ser Phe Leu Lys Thr Ile Gln Glu Val Ala Gly Tyr Val Leu
                 80                  85                  90

Ile Ala Leu Asn Thr Val Glu Arg Ile Pro Leu Glu Asn Leu Gln
                 95                 100                 105

Ile Ile Arg Gly Asn Met Tyr Tyr Glu Asn Ser Tyr Ala Leu Ala
                110                 115                 120

Val Leu Ser Asn Tyr Asp Ala Asn Lys Thr Gly Leu Lys Glu Leu
```

```
            125                 130                 135
Pro Met Arg Asn Leu Gln Glu Ile Leu His Gly Ala Val Arg Phe
            140                 145                 150
Ser Asn Asn Pro Ala Leu Cys Asn Val Glu Ser Ile Gln Trp Arg
            155                 160                 165
Asp Ile Val Ser Ser Asp Phe Leu Ser Asn Met Ser Met Asp Phe
            170                 175                 180
Gln Asn His Leu Gly Ser Cys Gln Lys Cys Asp Pro Ser Cys Pro
            185                 190                 195
Asn Gly Ser Cys Trp Gly Ala Gly Glu Asn Cys Gln Lys Leu
            200                 205                 210
Thr Lys Ile Ile Cys Ala Gln Gln Cys Ser Gly Arg Cys Arg Gly
            215                 220                 225
Lys Ser Pro Ser Asp Cys Cys His Asn Gln Cys Ala Ala Gly Cys
            230                 235                 240
Thr Gly Pro Arg Glu Ser Asp Cys Leu Val Cys Arg Lys Phe Arg
            245                 250                 255
Asp Glu Ala Thr Cys Lys Asp Thr Cys Pro Pro Leu Met Leu Tyr
            260                 265                 270
Asn Pro Thr Thr Tyr Gln Met Asp Val Asn Pro Glu Gly Lys Tyr
            275                 280                 285
Ser Phe Gly Ala Thr Cys Val Lys Lys Cys Pro Arg Asn Tyr Val
            290                 295                 300
Val Thr Asp His Gly Ser Cys Val Arg Ala Cys Gly Ala Asp Ser
            305                 310                 315
Tyr Glu Met Glu Glu Asp Gly Val Arg Lys Cys Lys Lys Cys Glu
            320                 325                 330
Gly Pro Cys Arg Lys Val Cys Asn Gly Ile Gly Ile Gly Glu Phe
            335                 340                 345
Lys Asp Ser Leu Ser Ile Asn Ala Thr Asn Ile Lys His Phe Lys
            350                 355                 360
Asn Cys Thr Ser Ile Ser Gly Asp Leu His Ile Leu Pro Val Ala
            365                 370                 375
Phe Arg Gly Asp Ser Phe Thr His Thr Pro Pro Leu Asp Pro Gln
            380                 385                 390
Glu Leu Asp Ile Leu Lys Thr Val Lys Glu Ile Thr Gly Phe Leu
            395                 400                 405
Leu Ile Gln Ala Trp Pro Glu Asn Arg Thr Asp Leu His Ala Phe
            410                 415                 420
Glu Asn Leu Glu Ile Ile Arg Gly Arg Thr Lys Gln His Gly Gln
            425                 430                 435
Phe Ser Leu Ala Val Val Ser Leu Asn Ile Thr Ser Leu Gly Leu
            440                 445                 450
Arg Ser Leu Lys Glu Ile Ser Asp Gly Asp Val Ile Ile Ser Gly
            455                 460                 465
Asn Lys Asn Leu Cys Tyr Ala Asn Thr Ile Asn Trp Lys Lys Leu
            470                 475                 480
Phe Gly Thr Ser Gly Gln Lys Thr Lys Ile Ile Ser Asn Arg Gly
            485                 490                 495
Glu Asn Ser Cys Lys Ala Thr Gly Gln Val Cys His Ala Leu Cys
            500                 505                 510
Ser Pro Glu Gly Cys Trp Gly Pro Glu Pro Arg Asp Cys Val Ser
            515                 520                 525
```

-continued

```
Cys Arg Asn Val Ser Arg Gly Arg Glu Cys Val Asp Lys Cys Asn
                530                 535                 540

Leu Leu Glu Gly Glu Pro Arg Glu Phe Val Glu Asn Ser Glu Cys
                545                 550                 555

Ile Gln Cys His Pro Glu Cys Leu Pro Gln Ala Met Asn Ile Thr
                560                 565                 570

Cys Thr Gly Arg Gly Pro Asp Asn Cys Ile Gln Cys Ala His Tyr
                575                 580                 585

Ile Asp Gly Pro His Cys Val Lys Thr Cys Pro Ala Gly Val Met
                590                 595                 600

Gly Glu Asn Asn Thr Leu Val Trp Lys Tyr Ala Asp Ala Gly His
                605                 610                 615

Val Cys His Leu Cys His Pro Asn Cys Thr Tyr Gly Cys Thr Gly
                620                 625                 630

Pro Gly Leu Glu Gly Cys Pro Thr Asn Gly Pro Lys Ile Pro Ser
                635                 640                 645

Ile Ala Thr Gly Met Val Gly Ala Leu Leu Leu Leu Leu Val Val
                650                 655                 660

Ala Leu Gly Ile Gly Leu Phe Met Arg Arg Arg His Ile Val Arg
                665                 670                 675

Lys Arg Thr Leu Arg Arg Leu Leu Gln Glu Arg Glu Leu Val Glu
                680                 685                 690

Pro Leu Thr Pro Ser Gly Glu Ala Pro Asn Gln Ala Leu Leu Arg
                695                 700                 705

Ile Leu Lys Glu Thr Glu Phe Lys Lys Ile Lys Val Leu Gly Ser
                710                 715                 720

Gly Ala Phe Gly Thr Val Tyr Lys Gly Leu Trp Ile Pro Glu Gly
                725                 730                 735

Glu Lys Val Lys Ile Pro Val Ala Ile Lys Glu Leu Arg Glu Ala
                740                 745                 750

Thr Ser Pro Lys Ala Asn Lys Glu Ile Leu Asp Glu Ala Tyr Val
                755                 760                 765

Met Ala Ser Val Asp Asn Pro His Val Cys Arg Leu Leu Gly Ile
                770                 775                 780

Cys Leu Thr Ser Thr Val Gln Leu Ile Thr Gln Leu Met Pro Phe
                785                 790                 795

Gly Cys Leu Leu Asp Tyr Val Arg Glu His Lys Asp Asn Ile Gly
                800                 805                 810

Ser Gln Tyr Leu Leu Asn Trp Cys Val Gln Ile Ala Lys Gly Met
                815                 820                 825

Asn Tyr Leu Glu Asp Arg Arg Leu Val His Arg Asp Leu Ala Ala
                830                 835                 840

Arg Asn Val Leu Val Lys Thr Pro Gln His Val Lys Ile Thr Asp
                845                 850                 855

Phe Gly Leu Ala Lys Leu Leu Gly Ala Glu Glu Lys Glu Tyr His
                860                 865                 870

Ala Glu Gly Gly Lys Val Pro Ile Lys Trp Met Ala Leu Glu Ser
                875                 880                 885

Ile Leu His Arg Ile Tyr Thr His Gln Ser Asp Val Trp Ser Tyr
                890                 895                 900

Gly Val Thr Val Trp Glu Leu Met Thr Phe Gly Ser Lys Pro Tyr
                905                 910                 915

Asp Gly Ile Pro Ala Ser Glu Ile Ser Ser Ile Leu Glu Lys Gly
                920                 925                 930
```

-continued

Glu Arg Leu Pro Gln Pro Pro Ile Cys Thr Ile Asp Val Tyr Met
                935                 940                 945

Ile Met Val Lys Cys Trp Met Ile Asp Ala Asp Ser Arg Pro Lys
                950                 955                 960

Phe Arg Glu Leu Ile Ile Glu Phe Ser Lys Met Ala Arg Asp Pro
                965                 970                 975

Gln Arg Tyr Leu Val Ile Gln Gly Asp Glu Arg Met His Leu Pro
                980                 985                 990

Ser Pro Thr Asp Ser Asn Phe Tyr Arg Ala Leu Met Asp Glu Glu
                995                 1000                1005

Asp Met Asp Asp Val Val Asp Ala Asp Glu Tyr Leu Ile Pro Gln
                1010                1015                1020

Gln Gly Phe Phe Ser Ser Pro Ser Thr Ser Arg Thr Pro Leu Leu
                1025                1030                1035

Ser Ser Leu Ser Ala Thr Ser Asn Asn Ser Thr Val Ala Cys Ile
                1040                1045                1050

Asp Arg Asn Gly Leu Gln Ser Cys Pro Ile Lys Glu Asp Ser Phe
                1055                1060                1065

Leu Gln Arg Tyr Ser Ser Asp Pro Thr Gly Ala Leu Thr Glu Asp
                1070                1075                1080

Ser Ile Asp Asp Thr Phe Leu Pro Val Pro Glu Tyr Ile Asn Gln
                1085                1090                1095

Ser Val Pro Lys Arg Pro Ala Gly Ser Val Gln Asn Pro Val Tyr
                1100                1105                1110

His Asn Gln Pro Leu Asn Pro Ala Pro Ser Arg Asp Pro His Tyr
                1115                1120                1125

Gln Asp Pro His Ser Thr Ala Val Gly Asn Pro Glu Tyr Leu Asn
                1130                1135                1140

Thr Val Gln Pro Thr Cys Val Asn Ser Thr Phe Asp Ser Pro Ala
                1145                1150                1155

His Trp Ala Gln Lys Gly Ser His Gln Ile Ser Leu Asp Asn Pro
                1160                1165                1170

Asp Tyr Gln Gln Asp Phe Phe Pro Lys Glu Ala Lys Pro Asn Gly
                1175                1180                1185

Ile Phe Lys Gly Ser Thr Ala Glu Asn Ala Glu Tyr Leu Arg Val
                1190                1195                1200

Ala Pro Gln Ser Ser Glu Phe Ile Gly Ala
                1205                1210

<210> SEQ ID NO 2
<211> LENGTH: 5616
<212> TYPE: DNA
<213> ORGANISM: Homo sapiens

<400> SEQUENCE: 2
ccccggcgca gcgcggccgc agcagcctcc gcccccgca cggtgtgagc          50 gcccgacgcg gccgaggcgg ccggagtccc gagctagccc cggcggccgc         100
cgccgcccag accggacgac aggccacctc gtcggcgtcc gcccgagtcc         150
ccgcctcgcc gccaacgcca caaccaccgc gcacggcccc ctgactccgt         200
ccagtattga tcgggagagc cggagcgagc tcttcgggga gcagcgatgc         250
gaccctccgg gacggccggg gcagcgctcc tggcgctgct ggctgcgctc         300
tgcccggcga gtcgggctct ggaggaaaag aaagtttgcc aaggcacgag         350

```
taacaagctc acgcagttgg gcacttttga agatcatttt ctcagcctcc      400
agaggatgtt caataactgt gaggtggtcc ttgggaattt ggaaattacc      450
tatgtgcaga ggaattatga tctttccttc ttaaagacca tccaggaggt     500
ggctggttat gtcctcattg ccctcaacac agtggagcga attcctttgg     550
aaaacctgca gatcatcaga ggaaatatgt actacgaaaa ttcctatgcc     600
ttagcagtct tatctaacta tgatgcaaat aaaaccggac tgaaggagct     650
gcccatgaga aatttacagg aaatcctgca tggcgccgtg cggttcagca     700
acaaccctgc cctgtgcaac gtggagagca tccagtggcg ggacatagtc     750
agcagtgact ttctcagcaa catgtcgatg gacttccaga accacctggg     800
cagctgccaa aagtgtgatc caagctgtcc aatgggagc tgctggggtg      850
caggagagga gaactgccag aaactgacca aaatcatctg tgcccagcag     900
tgctccgggc gctgccgtgg caagtccccc agtgactgct gccacaacca     950
gtgtgctgca ggctgcacag gcccccggga gagcgactgc ctggtctgcc    1000
gcaaattccg agacgaagcc acgtgcaagg acacctgccc cccactcatg    1050
ctctacaacc ccaccacgta ccagatggat gtgaaccccg agggcaaata    1100
cagctttggt gccacctgcg tgaagaagtg tccccgtaat tatgtggtga    1150
cagatcacgg ctcgtgcgtc cgagcctgtg gggccgacag ctatgagatg    1200
gaggaagacg gcgtccgcaa gtgtaagaag tgcgaagggc cttgccgcaa    1250
agtgtgtaac ggaataggta ttggtgaatt taaagactca ctctccataa    1300
atgctacgaa tattaaacac ttcaaaaact gcacctccat cagtggcgat    1350
ctccacatcc tgccggtggc atttagggt gactccttca cacatactcc     1400
tcctctggat ccacaggaac tggatattct gaaaaccgta aaggaaatca    1450
cagggttttt gctgattcag gcttggcctg aaaacaggac ggacctccat    1500
gcctttgaga acctagaaat catacgcggc aggaccaagc aacatggtca    1550
gttttctctt gcagtcgtca gcctgaacat aacatccttg ggattacgct    1600
ccctcaagga gataagtgat ggagatgtga taatttcagg aaacaaaaat    1650
ttgtgctatg caaatacaat aaactggaaa aaactgtttg ggacctccgg    1700
tcagaaaacc aaaattataa gcaacagagg tgaaaacagc tgcaaggcca    1750
caggccaggt ctgccatgcc ttgtgctccc ccgagggctg ctgggcccg     1800
gagcccaggg actgcgtctc ttgccggaat gtcagccgag caggaatg      1850
cgtggacaag tgcaaccttc tggagggtga gccaaggga tttgtggaga     1900
actctgagtg catacagtgc cacccagagt gcctgcctca ggccatgaac    1950
atcacctgca caggacgggg accagacaac tgtatccagt gtgcccacta    2000
cattgacggc cccactgcg tcaagacctg cccggcagga gtcatgggag      2050
aaaacaacac cctggtctgg aagtacgcag acgccggcca tgtgtgccac    2100
ctgtgccatc caaactgcac ctacggatgc actgggccag gtcttgaagg    2150
ctgtccaacg aatgggccta agatcccgtc catcgccact gggatggtgg    2200
gggccctcct cttgctgctg gtggtggccc tggggatcgg cctcttcatg    2250
cgaaggcgcc acatcgttcg gaagcgcacg ctgcggaggc tgctgcagga    2300
gagggagctt gtggagcctc ttacacccag tggagaagct cccaaccaag    2350
```

```
ctctcttgag gatcttgaag gaaactgaat tcaaaaagat caaagtgctg      2400
ggctccggtg cgttcggcac ggtgtataag ggactctgga tcccagaagg      2450
tgagaaagtt aaaattcccg tcgctatcaa ggaattaaga gaagcaacat      2500
ctccgaaagc caacaaggaa atcctcgatg aagcctacgt gatggccagc      2550
gtggacaacc cccacgtgtg ccgcctgctg ggcatctgcc tcacctccac      2600
cgtgcagctc atcacgcagc tcatgccctt cggctgcctc ctggactatg      2650
tccgggaaca caaagacaat attggctccc agtacctgct caactggtgt      2700
gtgcagatcg caagggcat gaactacttg gaggaccgtc gcttggtgca       2750
ccgcgacctg gcagccagga acgtactggt gaaaacaccg cagcatgtca      2800
agatcacaga ttttgggctg gccaaactgc tgggtgcgga agagaaagaa      2850
taccatgcag aaggaggcaa agtgcctatc aagtggatgg cattggaatc      2900
aattttacac agaatctata cccaccagag tgatgtctgg agctacgggg      2950
tgaccgtttg ggagttgatg acctttggat ccaagccata tgacggaatc      3000
cctgccagcg agatctcctc catcctggag aaaggagaac gcctccctca      3050
gccacccata tgtaccatcg atgtctacat gatcatggtc aagtgctgga      3100
tgatagacgc agatagtcgc ccaaagttcc gtgagttgat catcgaattc      3150
tccaaaatgg cccgagaccc ccagcgctac cttgtcattc aggggga tga     3200 aagaatgcat ttgccaagtc ctacagactc caacttctac cgtgccctga      3250
tggatgaaga agacatggac gacgtggtgg atgccgacga gtacctcatc      3300
ccacagcagg gcttcttcag cagccccctcc acgtcacgga ctcccctcct     3350
gagctctctg agtgcaacca gcaacaattc caccgtggct tgcattgata      3400
gaaatgggct gcaaagctgt cccatcaagg aagacagctt cttgcagcga      3450
tacagctcag accccacagg cgccttgact gaggacagca tagacgacac      3500
cttcctccca gtgcctgaat acataaacca gtccgttccc aaaaggcccg      3550
ctggctctgt gcagaatcct gtctatcaca atcagcctct gaaccccgcg      3600
cccagcagag acccacacta ccaggacccc cacagcactg cagtgggcaa      3650
ccccgagtat ctcaacactg tccagcccac ctgtgtcaac agcacattcg      3700
acagccctgc ccactgggcc cagaaaggca gccaccaaat tagcctggac      3750
aaccctgact accagcagga cttctttccc aaggaagcca agccaaatgg      3800
catctttaag ggctccacag ctgaaaatgc agaataccta agggtcgcgc      3850
cacaaagcag tgaatttatt ggagcatgac cacggaggat agtatgagcc      3900
ctaaaaatcc agactctttc gatacccagg accaagccac agcaggtcct      3950
ccatcccaac agccatgccc gcattagctc ttagacccac agactggttt      4000
tgcaacgttt acaccgacta gccaggaagt acttccacct cgggcacatt      4050
ttgggaagtt gcattccttt gtcttcaaac tgtgaagcat ttacagaaac      4100
gcatccagca agaatattgt cccttttgagc agaaatttat ctttcaaaga     4150
ggtatatttg aaaaaaaaaa aaagtatatg tgaggatttt tattgattgg      4200
ggatcttgga gttttttcatt gtcgctattg attttttactt caatgggctc    4250 ttccaacaag gaagaagctt gctggtagca cttgctaccc tgagttcatc      4300
caggcccaac tgtgagcaag gagcacaagc cacaagtctt ccagaggatg      4350
```

|  |  |
|---|---|
| cttgattcca gtggttctgc ttcaaggctt ccactgcaaa acactaaaga | 4400 |
| tccaagaagg ccttcatggc cccagcaggc cggatcggta ctgtatcaag | 4450 |
| tcatggcagg tacagtagga taagccactc tgtcccttcc tgggcaaaga | 4500 |
| agaaacggag gggatggaat tcttccttag acttactttt gtaaaaatgt | 4550 |
| ccccacggta cttactcccc actgatggac cagtggtttc cagtcatgag | 4600 |
| cgttagactg acttgtttgt cttccattcc attgttttga aactcagtat | 4650 |
| gctgcccctg tcttgctgtc atgaaatcag caagagagga tgacacatca | 4700 |
| aataataact cggattccag cccacattgg attcatcagc atttggacca | 4750 |
| atagcccaca gctgagaatg tggaatacct aaggatagca ccgcttttgt | 4800 |
| tctcgcaaaa acgtatctcc taatttgagg ctcagatgaa atgcatcagg | 4850 |
| tcctttgggg catagatcag aagactacaa aaatgaagct gctctgaaat | 4900 |
| ctcctttagc catcacccca accccccaaa attagtttgt gttacttatg | 4950 |
| gaagatagtt ttctcctttt acttcacttc aaaagctttt tactcaaaga | 5000 |
| gtatatgttc cctccaggtc agctgccccc aaacccsctc cttacgcttt | 5050 |
| gtcacacaaa aagtgtctct gccttgagtc atctattcaa gcacttacag | 5100 |
| ctctggccac aacagggcat tttacaggtg cgaatgacag tagcattatg | 5150 |
| agtagtgtgg aattcaggta gtaaatatga aactagggtt tgaaattgat | 5200 |
| aatgctttca caacatttgc agatgtttta gaaggaaaaa agttccttcc | 5250 |
| taaaataatt tctctacaat tggaagattg gaagattcag ctagttagga | 5300 |
| gcccacctt tttcctaatc tgtgtgtgcc ctgtaacctg actggttaac | 5350 |
| agcagtcctt tgtaaacagt gttttaaact ctcctagtca atatccaccc | 5400 |
| catccaattt atcaaggaag aaatggttca gaaaatattt tcagcctaca | 5450 |
| gttatgttca gtcacacaca catacaaaat gttccttttg cttttaaagt | 5500 |
| aatttttgac tcccagatca gtcagagccc ctacagcatt gttaagaaag | 5550 |
| tatttgattt ttgtctcaat gaaaataaaa ctatattcat ttccactcta | 5600 |
| aaaaaaaaaa aaaaaa | 5616 |

<210> SEQ ID NO 3
<211> LENGTH: 6
<212> TYPE: PRT
<213> ORGANISM: Homo sapiens

<400> SEQUENCE: 3

Lys Val Leu Gly Ser Gly
 1               5

<210> SEQ ID NO 4
<211> LENGTH: 18
<212> TYPE: DNA
<213> ORGANISM: Homo sapiens

<400> SEQUENCE: 4
aaagtgctgg gctccggt                                                  18

<210> SEQ ID NO 5
<211> LENGTH: 18
<212> TYPE: DNA
<213> ORGANISM: Homo sapiens

<400> SEQUENCE: 5

```
aaagtgctgt gctccggt                                           18

<210> SEQ ID NO 6
<211> LENGTH: 6
<212> TYPE: PRT
<213> ORGANISM: Homo sapiens

<400> SEQUENCE: 6

Lys Val Leu Ala Ser Gly
  1               5

<210> SEQ ID NO 7
<211> LENGTH: 18
<212> TYPE: DNA
<213> ORGANISM: Homo sapiens

<400> SEQUENCE: 7
aaagtgctgg cctccggt                                           18

<210> SEQ ID NO 8
<211> LENGTH: 6
<212> TYPE: PRT
<213> ORGANISM: Homo sapiens

<400> SEQUENCE: 8

Lys Val Leu Cys Ser Gly
  1               5

<210> SEQ ID NO 9
<211> LENGTH: 19
<212> TYPE: PRT
<213> ORGANISM: Homo sapiens

<400> SEQUENCE: 9

Ala Ile Lys Glu Leu Arg Glu Ala Thr Ser Pro Lys Ala Asn Lys
  1               5                  10                  15

Glu Ile Leu Asp

<210> SEQ ID NO 10
<211> LENGTH: 57
<212> TYPE: DNA
<213> ORGANISM: Homo sapiens

<400> SEQUENCE: 10
gctatcaagg aattaagaga agcaacatct ccgaaagcca acaaggaaat         50
cctcgat                                                       57

<210> SEQ ID NO 11
<211> LENGTH: 42
<212> TYPE: DNA
<213> ORGANISM: Homo sapiens

<400> SEQUENCE: 11
gctatcaaaa catctccgaa agccaacaag gaaatcctcg at                 42

<210> SEQ ID NO 12
<211> LENGTH: 48
<212> TYPE: DNA
<213> ORGANISM: Homo sapiens

<400> SEQUENCE: 12
gctatcaagc aaccaacatc tccgaaagcc aacaaggaaa tcctcgat           48
```

```
<210> SEQ ID NO 13
<211> LENGTH: 39
<212> TYPE: DNA
<213> ORGANISM: Homo sapiens

<400> SEQUENCE: 13
gctatcaagg aatcgaaagc caacaaggaa atcctcgat                        39

<210> SEQ ID NO 14
<211> LENGTH: 33
<212> TYPE: DNA
<213> ORGANISM: Homo sapiens

<400> SEQUENCE: 14
gctatcaagg aattaagaga agcaaccctc gat                              33

<210> SEQ ID NO 15
<211> LENGTH: 57
<212> TYPE: DNA
<213> ORGANISM: Homo sapiens

<400> SEQUENCE: 15
gctatcaagg aattaagaga agcaacatct ccgaaagtca acaaggaaat            50
cctcgat                                                           57

<210> SEQ ID NO 16
<211> LENGTH: 57
<212> TYPE: DNA
<213> ORGANISM: Homo sapiens

<400> SEQUENCE: 16
gctatcaagg aatcaagaga agcaacatct ccgaaagcca acaaggaaat            50
cctcgat                                                           57

<210> SEQ ID NO 17
<211> LENGTH: 57
<212> TYPE: DNA
<213> ORGANISM: Homo sapiens

<400> SEQUENCE: 17
gctatcaaga aattaagaga agcaacatct ccgaaagcca acaaggaaat            50
cctcgat                                                           57

<210> SEQ ID NO 18
<211> LENGTH: 7
<212> TYPE: PRT
<213> ORGANISM: Homo sapiens

<400> SEQUENCE: 18

Met Ala Ser Val Asp Asn Pro
 1               5

<210> SEQ ID NO 19
<211> LENGTH: 21
<212> TYPE: DNA
<213> ORGANISM: Homo sapiens

<400> SEQUENCE: 19
atggccagcg tggacaaccc c                                           21

<210> SEQ ID NO 20
<211> LENGTH: 27
```

```
<212> TYPE: DNA
<213> ORGANISM: Homo sapiens

<400> SEQUENCE: 20
atggccatag ccagcgtgga caacccc                                         27

<210> SEQ ID NO 21
<211> LENGTH: 9
<212> TYPE: PRT
<213> ORGANISM: Homo sapiens

<400> SEQUENCE: 21

Met Ala Ile Ala Ser Val Asp Asn Pro
  1               5

<210> SEQ ID NO 22
<211> LENGTH: 30
<212> TYPE: DNA
<213> ORGANISM: Homo sapiens

<400> SEQUENCE: 22
atggccagcg tggccagcgt ggataacccc                                      30

<210> SEQ ID NO 23
<211> LENGTH: 10
<212> TYPE: PRT
<213> ORGANISM: Homo sapiens

<400> SEQUENCE: 23

Met Ala Ser Val Ala Ser Val Asp Asn Pro
  1               5                  10

<210> SEQ ID NO 24
<211> LENGTH: 21
<212> TYPE: DNA
<213> ORGANISM: Homo sapiens

<400> SEQUENCE: 24
atggccatcg tggacaaccc c                                               21

<210> SEQ ID NO 25
<211> LENGTH: 7
<212> TYPE: PRT
<213> ORGANISM: Homo sapiens

<400> SEQUENCE: 25

Met Ala Ile Val Asp Asn Pro
  1               5

<210> SEQ ID NO 26
<211> LENGTH: 6
<212> TYPE: PRT
<213> ORGANISM: Homo sapiens

<400> SEQUENCE: 26

Phe Gly Leu Ala Lys Leu
  1               5

<210> SEQ ID NO 27
<211> LENGTH: 18
<212> TYPE: DNA
<213> ORGANISM: Homo sapiens

<400> SEQUENCE: 27
tttgggctgg ccaaactg                                                   18
```

<210> SEQ ID NO 28
<211> LENGTH: 18
<212> TYPE: DNA
<213> ORGANISM: Homo sapiens

<400> SEQUENCE: 28
tttgggcggg ccaaactg                                                 18

<210> SEQ ID NO 29
<211> LENGTH: 6
<212> TYPE: PRT
<213> ORGANISM: Homo sapiens

<400> SEQUENCE: 29

Phe Gly Arg Ala Lys Leu
 1               5

<210> SEQ ID NO 30
<211> LENGTH: 18
<212> TYPE: DNA
<213> ORGANISM: Homo sapiens

<400> SEQUENCE: 30
tttgggccgg ccaaactg                                                 18

<210> SEQ ID NO 31
<211> LENGTH: 6
<212> TYPE: PRT
<213> ORGANISM: Homo sapiens

<400> SEQUENCE: 31

Phe Gly Pro Ala Lys Leu
 1               5

<210> SEQ ID NO 32
<211> LENGTH: 10
<212> TYPE: DNA
<213> ORGANISM: Homo sapiens

<400> SEQUENCE: 32
ggaattaaga                                                          10

<210> SEQ ID NO 33
<211> LENGTH: 15
<212> TYPE: DNA
<213> ORGANISM: Homo sapiens

<400> SEQUENCE: 33
ggaattaaga gaagc                                                    15

<210> SEQ ID NO 34
<211> LENGTH: 18
<212> TYPE: DNA
<213> ORGANISM: Homo sapiens

<400> SEQUENCE: 34
taagagaagc aacatctc                                                 18

<210> SEQ ID NO 35
<211> LENGTH: 18
<212> TYPE: DNA
<213> ORGANISM: Homo sapiens

<400> SEQUENCE: 35

```
ttaagagaag caacatct                                                    18

<210> SEQ ID NO 36
<211> LENGTH: 12
<212> TYPE: DNA
<213> ORGANISM: Homo sapiens

<400> SEQUENCE: 36
taagagaagc aa                                                          12

<210> SEQ ID NO 37
<211> LENGTH: 24
<212> TYPE: DNA
<213> ORGANISM: Homo sapiens

<400> SEQUENCE: 37
atctccgaaa gccaacaagg aaat                                             24

<210> SEQ ID NO 38
<211> LENGTH: 19
<212> TYPE: PRT
<213> ORGANISM: Homo sapiens

<400> SEQUENCE: 38

Lys Lys Lys Gly Pro Trp Leu Glu Glu Glu Glu Ala Tyr Gly
 1               5                  10                  15

Trp Leu Asp Phe

<210> SEQ ID NO 39
<211> LENGTH: 25
<212> TYPE: DNA
<213> ORGANISM: Homo sapiens

<400> SEQUENCE: 39
caaatgagct ggcaagtgcc gtgtc                                            25

<210> SEQ ID NO 40
<211> LENGTH: 25
<212> TYPE: DNA
<213> ORGANISM: Homo sapiens

<400> SEQUENCE: 40
gagtttccca aacactcagt gaaac                                            25

<210> SEQ ID NO 41
<211> LENGTH: 25
<212> TYPE: DNA
<213> ORGANISM: Homo sapiens

<400> SEQUENCE: 41
gcaatatcag ccttaggtgc ggctc                                            25

<210> SEQ ID NO 42
<211> LENGTH: 26
<212> TYPE: DNA
<213> ORGANISM: Homo sapiens

<400> SEQUENCE: 42
catagaaagt gaacatttag gatgtg                                           26

<210> SEQ ID NO 43
<211> LENGTH: 24
<212> TYPE: DNA
```

<213> ORGANISM: Homo sapiens

<400> SEQUENCE: 43
ccatgagtac gtattttgaa actc                                24

<210> SEQ ID NO 44
<211> LENGTH: 24
<212> TYPE: DNA
<213> ORGANISM: Homo sapiens

<400> SEQUENCE: 44
catatcccca tggcaaactc ttgc                                24

<210> SEQ ID NO 45
<211> LENGTH: 24
<212> TYPE: DNA
<213> ORGANISM: Homo sapiens

<400> SEQUENCE: 45
ctaacgttcg ccagccataa gtcc                                24

<210> SEQ ID NO 46
<211> LENGTH: 26
<212> TYPE: DNA
<213> ORGANISM: Homo sapiens

<400> SEQUENCE: 46
gctgcgagct cacccagaat gtctgg                              26

<210> SEQ ID NO 47
<211> LENGTH: 44
<212> TYPE: DNA
<213> ORGANISM: Homo sapiens

<400> SEQUENCE: 47
tgtaaaacga cggccagtca agtgccgtgt cctggcaccc aagc          44

<210> SEQ ID NO 48
<211> LENGTH: 42
<212> TYPE: DNA
<213> ORGANISM: Homo sapiens

<400> SEQUENCE: 48
caggaaacag ctatgacccc aaacactcag tgaaacaaag ag            42

<210> SEQ ID NO 49
<211> LENGTH: 39
<212> TYPE: DNA
<213> ORGANISM: Homo sapiens

<400> SEQUENCE: 49
tgtaaaacga cggccagtcc ttaggtgcgg ctccacagc                39

<210> SEQ ID NO 50
<211> LENGTH: 40
<212> TYPE: DNA
<213> ORGANISM: Homo sapiens

<400> SEQUENCE: 50
caggaaacag ctatgaccca tttaggatgt ggagatgagc               40

<210> SEQ ID NO 51
<211> LENGTH: 41
<212> TYPE: DNA

```
<213> ORGANISM: Homo sapiens

<400> SEQUENCE: 51
tgtaaaacga cggccagtga aactcaagat cgcattcatg c        41

<210> SEQ ID NO 52
<211> LENGTH: 41
<212> TYPE: DNA
<213> ORGANISM: Homo sapiens

<400> SEQUENCE: 52
caggaaacag ctatgaccgc aaactcttgc tatcccagga g        41

<210> SEQ ID NO 53
<211> LENGTH: 40
<212> TYPE: DNA
<213> ORGANISM: Homo sapiens

<400> SEQUENCE: 53
tgtaaaacga cggccagtca gccataagtc ctcgacgtgg          40

<210> SEQ ID NO 54
<211> LENGTH: 42
<212> TYPE: DNA
<213> ORGANISM: Homo sapiens

<400> SEQUENCE: 54
caggaaacag ctatgaccca tcctcccctg catgtgttaa ac       42

<210> SEQ ID NO 55
<211> LENGTH: 23
<212> TYPE: DNA
<213> ORGANISM: Homo sapiens

<400> SEQUENCE: 55
tactggtgga gtatttgata gtg                            23

<210> SEQ ID NO 56
<211> LENGTH: 21
<212> TYPE: DNA
<213> ORGANISM: Homo sapiens

<400> SEQUENCE: 56
ctgtatcaaa gaatggtcct g                              21

<210> SEQ ID NO 57
<211> LENGTH: 38
<212> TYPE: DNA
<213> ORGANISM: Homo sapiens

<400> SEQUENCE: 57
tgtaaaacga cggccagtta gtgtattaac cttatgtg            38

<210> SEQ ID NO 58
<211> LENGTH: 42
<212> TYPE: DNA
<213> ORGANISM: Homo sapiens

<400> SEQUENCE: 58
caggaaacag ctatgaccac ctctattgtt ggatcatatt cg       42

<210> SEQ ID NO 59
<211> LENGTH: 18
<212> TYPE: DNA
```

```
<213> ORGANISM: Homo sapiens

<400> SEQUENCE: 59
tgtaaaacga cggccagt                                              18

<210> SEQ ID NO 60
<211> LENGTH: 18
<212> TYPE: DNA
<213> ORGANISM: Homo sapiens

<400> SEQUENCE: 60
caggaaacag ctatgacc                                              18
```

EGFR MUTATIONS

CROSS-REFERENCE TO RELATED APPLICATIONS

This application claims the benefit under 35 U.S.C. §119(e) of U.S. Provisional Patent Applications 60/577,425 filed Jun. 4, 2004, 60/635,344 filed Dec. 10, 2004, and 60/666,068 filed Mar. 28, 2005, which applications are hereby incorporated by reference in their entireties.

FIELD OF THE INVENTION

The present invention relates to cancer diagnostics and therapies and in particular to the detection of mutations that are diagnostic and/or prognostic.

BACKGROUND OF THE INVENTION

Epidermal Growth Factor Receptor (EGFR) is a member of the type 1 tyrosine kinase family of growth factor receptors, which play critical roles in cellular growth, differentiation, and survival. Activation of these receptors typically occurs via specific ligand binding, resulting in hetero- or homodimerization between receptor family members, with subsequent autophosphorylation of the tyrosine kinase domain. This activation triggers a cascade of intracellular signaling pathways involved in both cellular proliferation (the ras/raf/MAP kinase pathway) and survival (the PI3 kinase/Akt pathway). Members of this family, including EGFR and HER2, have been directly implicated in cellular transformation.

A number of human malignancies are associated with aberrant or over expression of EGFR and/or over expression of its specific ligands e.g. transforming growth factor a (Gullick, Br Med Bull 1991, 47:87-98; Modijtahedi and Dean, Int J Oncol 1994, 4:277-96; Salomon et al., Crit Rev Oncol Hematol 1995;19:183-232). EGFR over expression has been associated with an adverse prognosis in a number of human cancers, including NSCLC. In some instances, over expression of tumor EGFR has been correlated with both chemo resistance and a poor prognosis (Lei et al., Anticancer Res 1999; 19:221-8; Veale et al., Br J Cancer 1993;68:162-5). These observations suggest that agents that effectively inhibit EGFR receptor activation and subsequent downstream signaling may have clinical activity in a variety of human cancers, including NSCLC.

Tarceva™ (also known as erlotinib; OSI-774), a quinazoline, is an orally active, potent, selective inhibitor of EGFR tyrosine kinase. Erlotinib inhibits human EGFR tyrosine kinase with an $IC_{50}$ of 2 nM (0.786 mg/mL) in an in vitro enzyme assay. This inhibition is selective for EGFR tyrosine kinase, results in cell cycle arrest at $G_1$, and is reversible. Oral administration of erlotinib in mice has demonstrated a >70% reduction in EGFR autophosphorylation in human xenografts and marked growth inhibition of HN5 and A431 xenografts in nude mice has been demonstrated. In addition to single-agent activity in vivo assay systems, erlotinib has been evaluated in combination with a number of chemotherapy agents to determine possible interactions. There was an additive interaction between erlotinib and paclitaxel, cisplatin, gemcitabine, and doxorubicin.

Lung cancer represents the leading cause of cancer-related mortality for both men and women in the United States. In 2000, it was estimated that 164,000 new cases would be diagnosed and 157,000 patients would die from this disease (Greenlee et al., CA Cancer J Clin 2001, 51:15-36). Approximately 75% of these patients would have had non-small cell histologies, with the majority presenting with inoperable Stage IIIB or Stage IV disease. For those patients with more limited disease at presentation (Stages I-IIIA), relapse following standard surgical therapy, with or without adjuvant or neoadjuvant chemo- and/or radiotherapy, is common. These findings result in an overall 5-year survival in non-small cell lung cancer (NSCLC) of ~12% and serve to emphasize the unmet medical need in this disease.

The platinum compound cisplatin was the first chemotherapy agent to show clinical benefit in the management of locally advanced or metastatic NSCLC. Randomized clinical trials demonstrated improved response rates, quality of life, and survival compared with the best supportive care (Rapp et al. 1988). However, the magnitude of this improvement was modest—measured in weeks. Subsequently, a number of newer chemotherapy agents have been evaluated as single agents and in combination with the platinum salts in the first-line setting. The conclusion from these studies is that modern "doublet" chemotherapy appears to achieve response rates of 15%-20%, median time to disease progression of 3-4 months, and median survival of 7-8 months. The modest improvements in efficacy with combination therapies over the results obtained with cisplatin have established these therapies as a standard of care for patients with advanced NSCLC and an acceptable performance status (Non-Small Cell Lung Cancer Cooperative Group, Br Med J 1995, 311:899-909; American Society of Clinical Oncology, J Clin Oncol 1997, 15:2996-3018; Breathnach et al., J Clin Oncol 2001;19:1734-42).

SUMMARY OF THE INVENTION

According to an aspect of the invention there is provided a method for identifying a tumor in a human subject that is susceptible to treatment comprising determining the presence of a mutated EGFR gene or mutated EGFR protein in a sample of said tumor wherein said mutation is located in exons 18-21 of EGFR whereby the presence of a mutated EGFR gene or mutated EGFR protein indicates the tumor is susceptible to treatment.

In another aspect of the invention there is provided a method of treating a tumor in a mammal comprising identifying the presence of an EGFR mutation in said tumor and treating said mammal with an anticancer agent.

In another aspect of the invention there is provided method of identifying an EGFR mutation in a sample comprising contacting nucleic acid from said sample with a probe that is capable of specifically hybridizing to nucleic acid encoding a mutated EGFR protein, or fragment thereof incorporating a mutation, and detecting the hybridization.

In another aspect of the invention there is provided nucleic acid probes capable of specifically hybridizing to nucleic acid encoding a mutated EGFR protein or fragment thereof incorporating a mutation.

In another aspect of the invention there is provided a method of detecting a mutated EGFR gene in a sample comprising amplifying from said sample nucleic acid corresponding to the kinase domain of said EGFR gene, or a fragment thereof suspected of containing a mutation, and comparing the electrophoretic mobility of the amplified nucleic acid to the electrophoretic mobility of corresponding wild-type EGFR gene or fragment thereof.

In another aspect of the invention there is provided a method for identifying a tumor in a human subject that is susceptible to treatment with an EGFR inhibitor comprising (i) determining the presence of a wild-type KRAS protein or gene in a sample of said tumor whereby the presence of a wild-type KRAS protein or gene indicates that the tumor is susceptible to treatment with an EGFR inhibitor or (ii) determining the presence of a mutated KRAS protein or gene in a sample of said tumor whereby the absence of a mutated KRAS protein or gene indicates that the tumor is susceptible to treatment with an EGFR inhibitor.

BRIEF DESCRIPTION OF THE DRAWINGS

FIG. 1 illustrates the amino acid sequence of wild-type EGFR1 (SEQ ID NO: 1) in which the signal sequence is residues 1-24, the extracellular domain includes residues 24-645, the transmembrane domain includes residues 646-668, and the cytoplasmic domain includes residues 669-1210. The tyrosine kinase domain region is residues 718-964, and the threonine phosphorylation site is residue 678.

FIG. 2a through 2d is the cDNA sequence (SEQ ID NO: 2) of wild-type EGFR in which exon 18 corresponds to nucleotides 2308-2430; exon 19 corresponds to nucleotides 2431-2529; exon 20 corresponds to nucleotides 2530-2715 and exon 21 corresponds to 2716-2871.

FIG. 8 illustrates mutations in exons 18 and 19 of EGFR gene and protein sequences. Amino acid and nucleotide changes, and insertions are in bold, underlined font while deletions are shown as dashes (-).

FIG. 9 illustrates mutations in exons 20 and 21 of EGFR gene and protein sequences. Amino acid and nucleotide changes, and insertions are in bold, underlined font while deletions are shown as dashes (-).

DETAILED DESCRIPTION OF THE PREFERRED EMBODIMENTS

Figure 3:
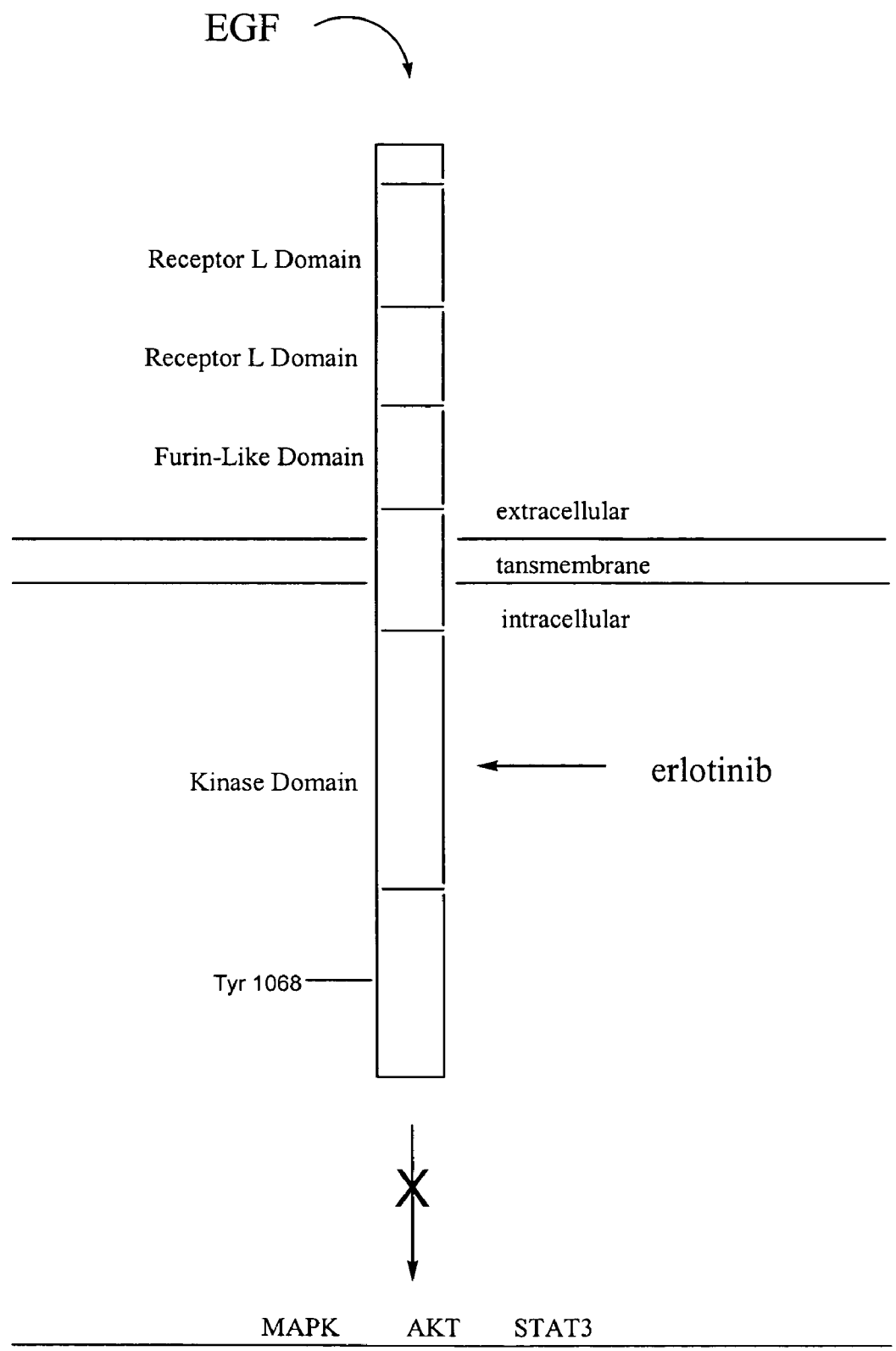
FIG. 3 is a graphical representation of extracellular (top) and intracellular (bottom) regions of EGFR.
Figure 4:
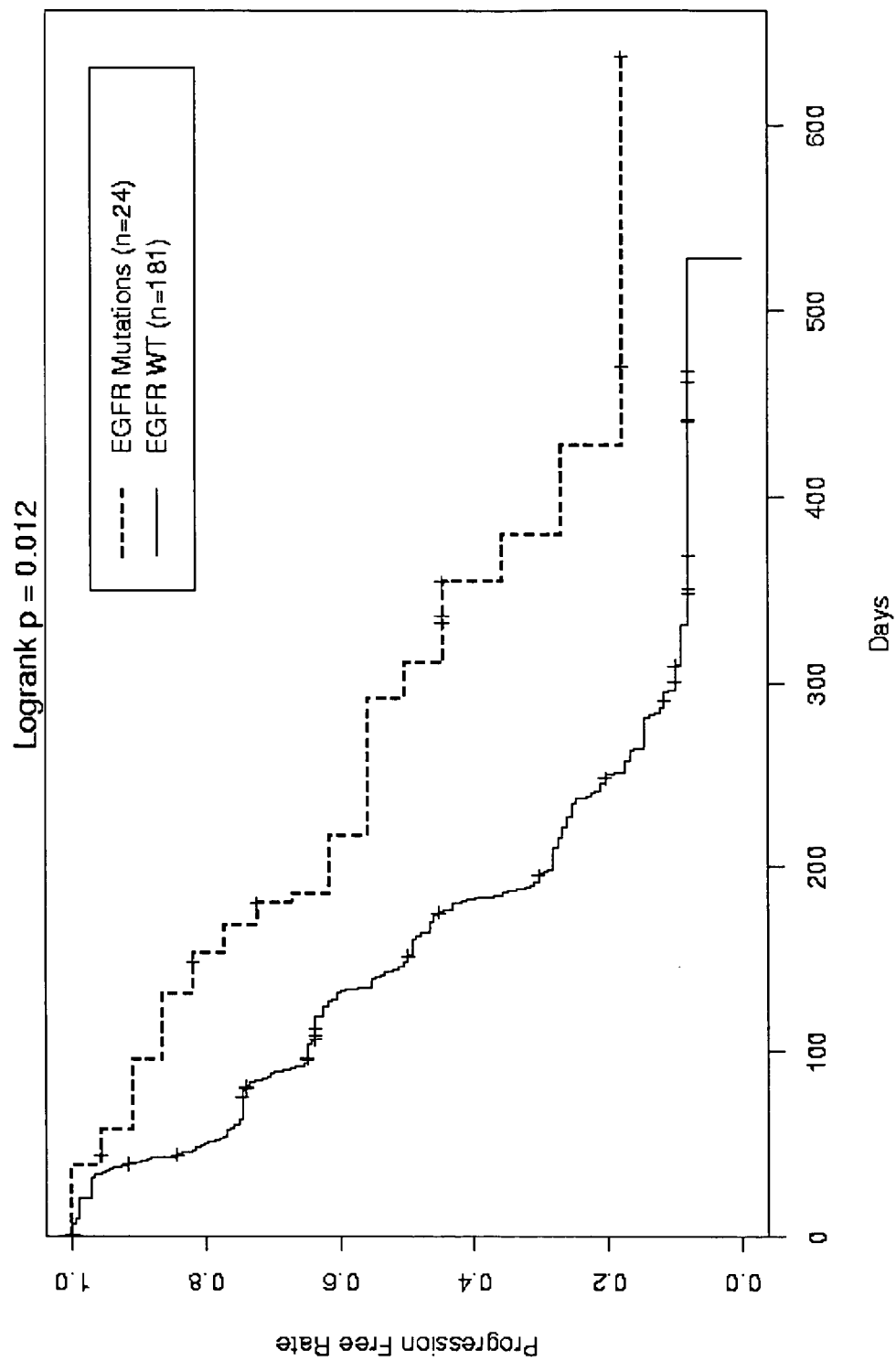
FIG. 4 is a Kaplan-Meier curve showing time to progression of patients having NSCLC tumors expressing wild-type EGFR (solid line) and mutant EGFR (dashed line).
Figure 5:
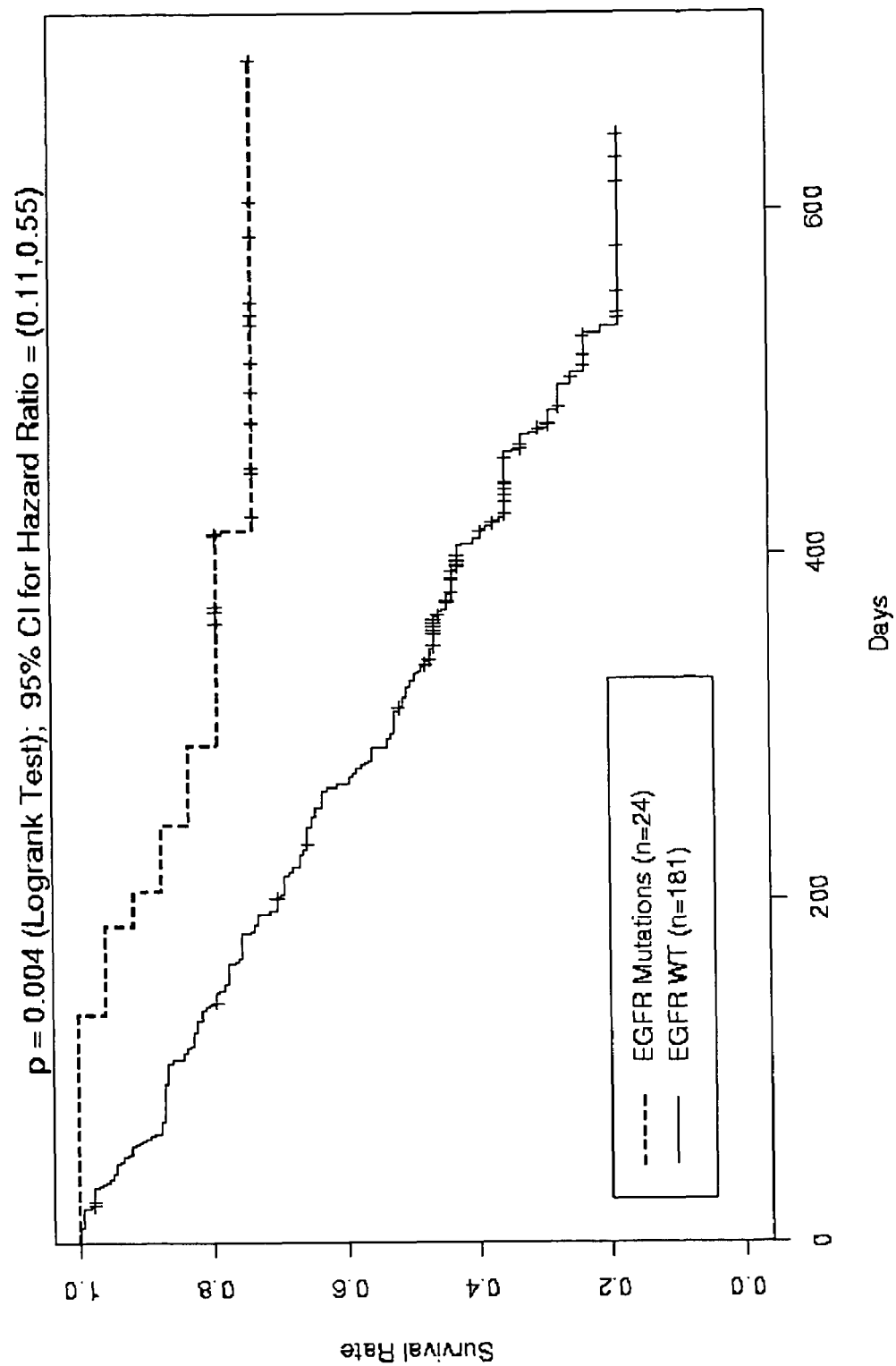
FIG. 5 is a Kaplan-Meier curve showing survival of patients having NSCLC tumors expressing wild-type EGFR (solid line) and mutant EGFR (dashed line).
Figure 6:
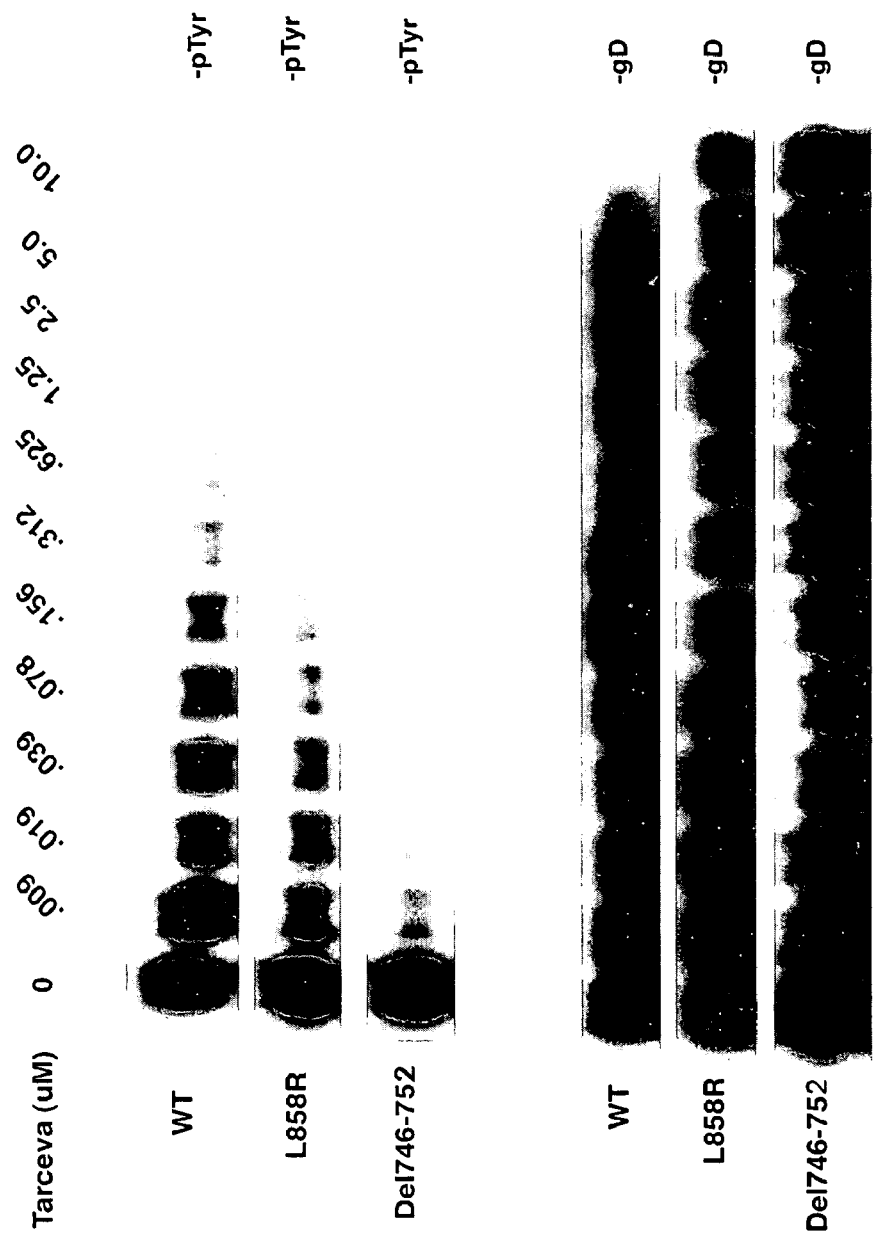
FIG. 6 is an autoradiograph illustrating inhibition of autophosphorylation of wild-type EGFR, and mutant EGFR (L858R and del746-752) with varying concentrations of erlotinib in transiently transfected COS7 cells.
Figure 7:
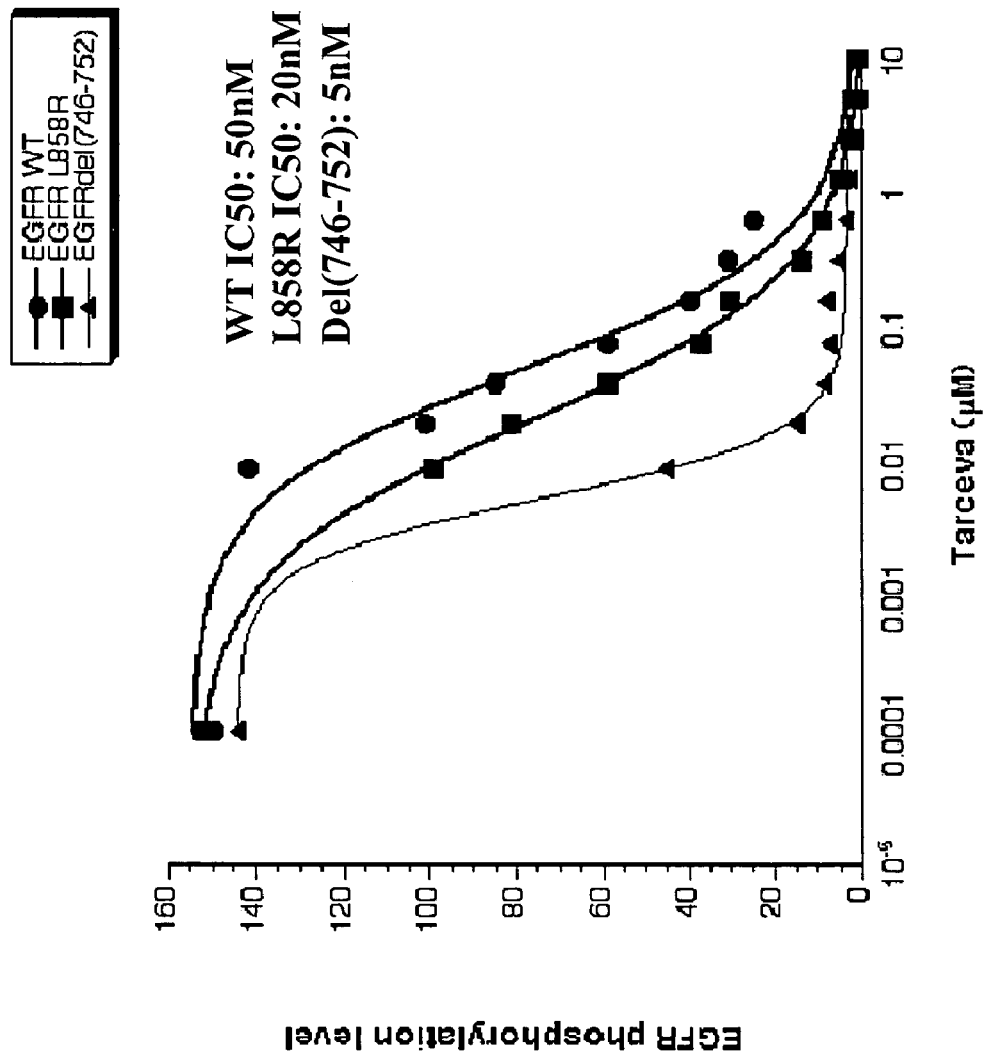
FIG. 7 is a graph showing inhibition of autophosphorylation of wild-type EGFR and mutant EGFR (L858R and del746-752) with varying concentrations of erlotinib in transiently transfected COS7 cells.

It is a discovery of the present invention that mutational events associated with tumorigenesis occur in Epidermal Growth Factor Receptor (EGFR). Although it was previously known that aberrant EGFR activity was associated with various cancers, it was unknown that mutations in the EGFR kinase domain region (KDR) existed that caused aberrant signaling activity associated with some cancers. Surprisingly patients suffering from tumors having EGFR KDR mutations have a better prognosis than those with wild-type EGFR. The KDR mutations of the EGFR gene can involve rearrangements such as insertions and deletions as well as point mutations.

Samples from approximately 250 patients who participated a randomized, double-blinded phase III clinical trial referred to as Tribute were sequenced for mutations occurring in exons 18-21 of EGFR. Tribute studied 1,079 patients at approximately 150 centers in the United States having histological confirmed NSCLC who had not received prior chemotherapy comparing erlotinib+chemotherapy (carboplatin/paclitaxel) with chemotherapy alone. Patients received paclitaxel (200 mg/m² 3 hour i.v. infusion) followed by carboplatin (AUC=6 mg/ml×minute infused over 15-30 minutes using Calvert formula) with or without erlotinib (100 mg/day p.o. escalated to 150mg/day for tolerant patients). Tumor samples, formalin-fixed paraffin-embedded blocks or unstained slides, from approximately 250 patients collected from the Tribute trial were enriched for tumor cells by laser capture mircrodissection followed by DNA extraction. Exons 18-21 were amplified by nested PCR and bi-directional sequences were obtained from each PCR product using fluorescent dye-terminator chemistry. Mutations discovered from the sequencing are shown in table 1:

TABLE 1

| protein mutation | nucleic acid mutation | exon |
|---|---|---|
| G719A | 2402G > C | 18 |
| G719C | 2401G > T | 18 |
| G719S | 2401G > A | 18 |
| E746-R748 del | 2482-2490 del GGAATTAAGA (SEQ ID NO: 32) | 19 |
| E746-A750 del | 2481-2495 del GGAATTAAGAGAAGC (SEQ ID NO: 33) | 19 |
| E746-R748 del E749Q A750P | 2482'2490 del GAATTAAGA 2491G > C 2494G > C | 19 |
| L747-E749 del A750P | 2485-2493 del TTAAGAGAA 494G > C | 19 |
| L747S R748-P753 del | 2486-2503 del TAAGAGAAGCAACATCTC (SEQ ID NO: 34) | 19 |

TABLE 1-continued

| protein mutation | nucleic acid mutation | exon |
|---|---|---|
| L747-S752 del<br>E746V | 2485-2502 del TTAAGAGAAGCAACATCT<br>2483A > T<br>(SEQ ID NO: 35) | 19 |
| L747-T751 del<br>ins S | 2486-2494 del TAAGAGAAGCAA (SEQ ID NO:<br>36) | 19 |
| S752-I759 del | 2499-2522 del ATCTCCGAAAGCCAACAAGGAAAT<br>(SEQ ID NO: 37) | 19 |
| M766-A767 AI ins | 2544-2545 ins GCCATA | 20 |
| S768-V769 SVA ins | 2554-2555 ins CCAGCGTGG (2556C > T<br>silent) | 20 |
| L858R | 2819T > G | 21 |
| G719C<br>S768I | 2401G > T<br>2549G > T {2607G > A SNP silent} | 18<br>20 |
| G719C<br>V765M<br>S768I | 2401G > T<br>2539G > A<br>2549G > T | 18<br>20<br>20 |
| A755V | 2510C > T | 19 |
| L747S | 2486T > C | 19 |
| E746K | 2482G > A | 19 |
| P772-H773 V ins | 2561-2562 ins GGT | 20 |
| L858P | 2819T > C | 21 |
| L861Q | 2576T > A | 21 |
| P772-H773 NS ins<br>H773Y | 2562-2563 ins AACTCC<br>2563C > T | 20 |
| T790M<br>L858R | 2615C > T<br>2819T > G | 20<br>21 |
| S784F<br>L858R | | 21<br>21 | ins = insertion
del = deletion

Nucleotide numbering for mutations is based on reference sequence shown in FIGS. 2a-2d.

Clinical outcome of patients having tumors with EGFR mutations and wild-type EGFR were analyzed according to response (complete+partial) benefit (response+stable disease) and progressive disease. Lesions were evaluated using Response Evaluation Criteria in Solid Tumors (RECIST) criteria whereby "complete response" (CR) is defined as the disappearance of all target lesions; "partial response" (PR) is defined as at least a 30% decrease in the sum of the longest diameter of target lesions, taking as reference the baseline sum longest diameter; "progressive disease" (PD) is defined as at least a 20% increase in the sum of the longest diameter of target lesions, taking as reference the smallest sum longest diameter recorded since the treatment started or the appearance of one or more new lesions; and "stable disease" (SD) is defined as neither sufficient shrinkage to qualify for partial response nor sufficient increase to qualify for progressive disease, taking as reference the smallest sum longest diameter since the treatment started.

Results of the analysis are summarized in table 2.

TABLE 2

| | Mutant EGFR<br>n = 24 | | Wild-Type EGFR<br>n = 181 | |
|---|---|---|---|---|
| | Response/Benefit Rate | | | |
| response (CR + PR) | 11 | 46% | 46 | 25% |
| benefit (CR + PR + SD) | 18 | 75% | 105 | 58% |
| SD | 7 | 29% | 59 | 33% |
| PD | 6 | 25% | 76 | 42% |
| | Survival (days) | | | |
| median | 435 | | 309 | |
| range | 133-687 | | 9-643 | |

CR = complete response;
PR = partial response;
SD = stable disease;
PD = progressing disease Analysis of clinical outcome revealed that patients with tumors expressing a mutation in exons 18-21 of EGFR have better prognosis than those with tumors expressing wild-type EGFR. Mutant EGFR patients exhibited greater response rate, benefit rate and survival when treated with chemotherapy or chemotherapy plus erlotinib. These results are useful for predicting outcome such that patients who's tumors have EGFR mutations in any or all of exons 18 through 21 have more favorable prognosis than patients who's tumors do not have such mutations.

Accordingly, the present invention provides a method for determining the prognosis of a patient having a tumor comprising determining in a sample of said tumor the presence or absence of one or more EGFR mutations in exons 18-21 (or the amino acid sequence corresponding to exons 18-21) whereby the presence of said one or more EGFR mutation indicates better prognosis compared to the absence of said one or more EGFR mutation. By "prognosis" is meant response and/or benefit and/or survival. By "EGFR mutations" means an amino acid or nucleic acid sequence that differs from wild-type EGFR protein or nucleic acid respectively found on one allele (heterozygous) or both alleles (homozygous) and may be somatic or germ line. In a particular embodiment said mutation is found in the kinase domain region (KDR) of EGFR. In another particular embodiment the mutation is an amino acid substitution, deletion or insertion as shown in table 1. In an embodiment the amino acid mutation is one or more of the following: G719A, E746K, L747S, E749Q, A750P, A755V, S7681, L858P, E746-R748 del, R748-P753 del, M766-A767 AI ins, and S768-V769 SVA ins. In another particular embodiment, the mutation is a nucleic acid point mutation, deletion or insertion as shown in table 1. In an embodiment, the nucleic acid mutation is one or more the following: 2402G>C; 2482G>A; 2486T>C; 2491G>C; 2494G>C; 2510C>T; 2549G>T; 2819T>C; 2482-2490 del; 2486-2503 del; 2544-2545 ins GCCATA; and 2554-2555 ins CCAGCGTGG.

EGFR exons 18-21 from an H1975 tumor cell line that exhibited resistance to treatment with erlotinib was sequenced and found to incorporate a mutation T790M in combination with an L858R mutation. Accordingly the present invention further provides a method for determining the prognosis of a patient having a tumor comprising determining in a sample of said tumor the presence or absence of the T790M EGFR mutation whereby the presence of said T790M EGFR mutation indicates poorer prognosis compared to the absence of said T790M EGFR mutation. Further, there is provided a method of identifying patients having a tumor that is less responsive to therapy of an EGFR inhibitor such as erlotinib or gefitinib, whether in combination with chemotherapy or not, comprising determining the presence or absence of a T790M EGFR mutation in the patient's tumor whereby the presence of said mutation indicates the patient will respond less to said therapy compared to a patient having a tumor that does not have said T790M EGFR mutation. Further, there is provided a method of identifying a tumor that is resistant to treatment with an EGFR inhibitor, such as a kinase domain binding inhibitor (for example erlotinib or gefitinib), whether in combination with chemotherapy or not, comprising determining the presence or absence of a T790M EGFR mutation in a sample of the tumor whereby the presence of said mutation indicates the tumor is resistant to said treatment. It is understood that determination of the mutation is at the protein level or nucleic acid level (genomic DNA or mRNA) and are accomplished using techniques such as those described herein. In a particular embodiment, said EGFR inhibitor competes with ATP at the EGFR kinase domain. In a particular embodiment the EGFR inhibitor is erlotinib.

In another aspect, there is provided a method of treating a patient having a tumor incorporating a T790M mutant EGFR protein or gene (or treating a tumor incorporating a T790M mutant EGFR protein or gene) comprising co-administering to said patient (or contacting said tumor with) a first compound that binds to and/or inhibits signaling of said T790M mutant EGFR in combination with a second compound that binds to and/or inhibits signaling of wild-type EGFR or EGFR incorporating an activating mutation. In a particular embodiment said activating mutation is one or more of those described in Table 1 (other than T790M). In a particular embodiment said first and second compounds are administered sequentially or concommitantly. In a particular embodiment said second compound is erlotinib.

In another aspect of the invention, there is provided a method of screening for compounds that inhibit signaling of a mutant EGFR protein that incorporates a T790M mutation, comprising contacting said mutant EGFR with a test compound in the presence of a phosphorylation substrate and ATP and detecting a change in the amount of phosphorylation of said substrate whereby a reduction of phosphorylation of said substrate compared to a control, or compared to phosphorylation of the substrate in the absence of the test compound, indicates said test compound is an inhibitor of mutant EGFR signaling. In an embodiment, said method is performed in vitro in the presence of a ligand for said mutant EGFR such as EGF or TGF-alpha.

In a particular embodiment the inhibitory activity of a test compound can be determined in vitro by the amount of inhibition of the phosphorylation of an exogenous substrate (e.g. $Lys_3$-Gastrin or polyGluTyr (4:1) random copolymer (I. Posner et. al., J. Biol. Chem. 267 (29), 20638-47 (1992)) on tyrosine by epidermal growth factor receptor kinase by a test compound relative to a control. Purified, soluble human T790M mutant EGFR (96 ng) is preincubated in a microfuge tube with EGF (2 μg/ml) in phosphorylation buffer+vanadate (PBV: 50 mM HEPES, pH 7.4; 125 mM NaCl; 24 mM $MgCl_2$; 100 μM sodium orthovanadate), in a total volume of 10 μl, for 20-30 minutes at room temperature. The test compound, dissolved in dimethylsulfoxide (DMSO), is diluted in PBV, and 10 μl is mixed with the mutant EGFR/EGF mix, and incubated for 10-30 minutes at 30° C. The phosphorylation reaction is initiated by addition of 20 μl $^{33}$ P-ATP/substrate mix (120 μM $Lys_3$-Gastrin (sequence in single letter code for amino acids, KKKGPWLEEEEEAYGWLDF—SEQ ID NO: 38), 50 mM Hepes pH 7.4, 40 μM ATP, 2 μCi γ-[$^{33}$P]-ATP) to the mutant EGFR/EGF mix and incubated for 20 minutes at room temperature. The reaction is stopped by addition of 10 μl stop solution (0.5M EDTA, pH 8; 2mM ATP) and 6 μl 2N HCl. The tubes are centrifuged at 14,000 RPM, 4° C., for 10 minutes. 35 μl of supernatant from each tube is pipetted onto a 2.5 cm circle of Whatman P81 paper, bulk washed four times in 5% acetic acid, 1 liter per wash, and then air dried. This results in the binding of substrate to the paper with loss of free ATP on washing. The [$^{33}$P] incorporated is measured by liquid scintillation counting. Incorporation in the absence of substrate (e.g., $lys_3$-gastrin) is subtracted from all values as a background and percent inhibition is calculated relative to controls without test compound present. Such assays, carried out with a range of doses of test compounds, allow the determination of an approximate $IC_{50}$ value for the in vitro inhibition of T790M mutant EGFR kinase activity.

In another aspect of the invention there is provided a method for identifying a tumor in a human subject that is susceptible to treatment comprising determining the presence of a mutated EGFR gene or mutated EGFR protein in a sample of said tumor wherein said mutation is located in exons 18-21 of EGFR whereby the presence of a mutated EGFR gene or mutated EGFR protein indicates that the tumor is susceptible to treatment with an anticancer agent. In a particular embodiment the anticancer agent is a chemotherapeutic agent which may be a cytotoxic or cytostatic. Tumors include neuroblastoma, intestine carcinoma such as rectum carcinoma, colon carcinoma, familiary adenomatous polyposis carcinoma and hereditary non-polyposis colorectal cancer, esophageal carcinoma, labial carcinoma, larynx carcinoma, hypopharynx carcinoma, tong carcinoma, salivary gland carcinoma, gastric carcinoma, adenocarcinoma, medullary thyroidea carcinoma, papillary thyroidea carcinoma, renal carcinoma, kidney parenchym carcinoma, ovarian carcinoma, cervix carcinoma, uterine corpus carcinoma, endometrium carcinoma, chorion carcinoma, pancreatic carcinoma, prostate carcinoma, testis carcinoma, breast carcinoma, urinary carcinoma, melanoma, brain tumors such as glioblastoma, astrocytoma, meningioma, medulloblastoma and peripheral neuroectodermal tumors, Hodgkin lymphoma, non-Hodgkin lymphoma, Burkitt lymphoma, acute lymphatic leukemia (ALL), chronic lymphatic leukemia (CLL), acute myeloid leukemia (AML), chronic myeloid leukemia (CML), adult T-cell leukemia lymphoma, hepatocellular carcinoma, gall bladder carcinoma, bronchial carcinoma, small cell lung carcinoma, non-small cell lung carcinoma, multiple myeloma, basalioma, teratoma, retinoblastoma, choroidea melanoma, seminoma, rhabdomyo sarcoma, craniopharyngeoma, osteosarcoma, chondrosarcoma, myosarcoma, liposarcoma, fibrosarcoma, Ewing sarcoma and plasmocytoma. Particular tumors include those of the brain, liver, kidney, bladder, breast, gastric, ovarian, colorectal, prostate, pancreatic, breast, lung, vulval, thyroid, colorectal, oesophageal, hepatic carcinomas, sarcomas, glioblastomas, head and neck, leukemias and lymphoid malignancies.

Particular chemotherapeutic agents include, but are not limited to (i) antimetabolites, such as cytarabine, fludarabine, 5-fluoro-2'-deoxyuiridine, gemcitabine, hydroxyurea or methotrexate; (ii) DNA-fragmenting agents, such as bleomycin, (iii) DNA-crosslinking agents, such as chlorambucil, cisplatin, cyclophosphamide or nitrogen mustard; (iv) intercalating agents such as adriamycin (doxorubicin) or mitoxantrone; (v) protein synthesis inhibitors, such as L-asparaginase, cycloheximide, puromycin or diphtheria toxin; (Vi) topoisomerase I poisons, such as camptothecin or topotecan; (vii) topoisomerase II poisons, such as etoposide (VP-16) or teniposide; (viii) microtubule-directed agents, such as colcemid, colchicine, paclitaxel, vinblastine or vincristine; (ix) kinase inhibitors such as flavopiridol, staurosporin, ST1571 (CPG 57148B) or UCN-01 (7-hydroxystaurosporine); (x)miscellaneous investigational agents such as thiopl-atin, PS-341, phenylbutyrate, ET-18- $OCH_3$, or farnesyl transferase inhibitors (L-739749, L-744832); polyphenols such as quercetin, resveratrol, piceatannol, epigallocatechine gallate, theaflavins, flavanols, procyanidins, betulinic acid and derivatives thereof; (xi) hormones such as glucocorticoids or fenretinide; (xii) hormone antagonists, such as tamoxifen, finasteride or LHRH antagonists. In an embodiment, the chemotherapeutic compound is one or more of gemcitabine, cisplatin, doxorubicin, daunarubicin, paclitexel, taxotere and mitomycin C. In a particular embodiment the chemotherapeutic compound is one or more of gemcitabine, cisplatin and paclitaxel. In another embodiment the treatment is an inhibitor of EGFR. In an embodiment the EGFR inhibitor is an antibody such as Erbitutux™ (cetuximab, Imclone Systems Inc.) and ABX-EGF (panitumumab, Abgenix, Inc.). In another embodiment the EGFR inhibitor is a small molecule that competes with ATP such as Tarceva™ (erlotinib, OSI Pharmaceuticals), Iressa™(gefitinib, AstraZeneca), tyrphostins described by Dvir, et al., J Cell Biol., 113:857-865(1991); tricyclic pyrimidine compounds disclosed in U.S. Pat. No. 5,679,683;compound 6 - (2,6- dichlorophenyl)-2-(4-(2-diethylaminoethoxy)phenylamino)-8-methyl-8H-pyrido(2,3- d)pyrimidin-7-one (known as PD166285) disclosed in Panek, et al., Journal of Pharmacology and Experimental Therapeutics 283, 1433-1444 (1997).

In another aspect of the invention there is provided a method of identifying an EGFR mutation in a sample comprising contacting nucleic acid from said sample with a nucleic acid probe that is capable of specifically hybridizing to nucleic acid encoding a mutated EGFR protein, or fragment thereof incorporating a mutation, and detecting said hybridization. In a particular embodiment said probe is detectably labeled such as with a radioisotope ($^3$H, $^{32}$P, $^{33}$P etc), a fluorescent agent (rhodamine, fluorescene etc.) or a chromogenic agent. In a particular embodiment the probe is an antisense oligomer, for example PNA, morpholino-phosphoramidates, LNA or 2'-alkoxyalkoxy. The probe may be from about 8 nucleotides to about 100 nucleotides, or about 10 to about 75, or about 15 to about 50, or about 20 to about 30. In another aspect said probes of the invention are provided in a kit for identifying EGFR mutations in a sample, said kit comprising an oligonucleotide that specifically hybridizes to or adjacent to a site of mutation in the EGFR gene. The kit may further comprise instructions for treating patients having tumors that contain EGFR mutations with an EGFR inhibitor based on the result of a hybridization test using the kit.

In another aspect of the invention there is provided a method of detecting a mutated EGFR gene in a sample comprising amplifying from said sample nucleic acid corresponding to the kinase domain of said EGFR gene, or exons 18-21, or a fragment thereof suspected of containing a mutation, and comparing the electrophoretic mobility of the amplified nucleic acid to the electrophoretic mobility of corresponding wild-type EGFR gene or fragment thereof. A difference in the mobility indicates the presence of a mutation in the amplified nucleic acid sequence. Electrophoretic mobility may be determined on polyacrylamide gel.

Alternatively, amplified EGFR gene or fragment nucleic acid may be analyzed for detection of mutations using Enzymatic Mutation Detection (EMD) (Del Tito et al, Clinical Chemistry 44:731-739, 1998). EMD uses the bacteriophage resolvase $T_4$ endonuclease VII, which scans along double-stranded DNA until it detects and cleaves structural distortions caused by base pair mismatches resulting from point mutations, insertions and deletions. Detection of two short fragments formed by resolvase cleavage, for example by gel eletrophoresis, indicates the presence of a mutation. Benefits of the EMD method are a single protocol to identify point mutations, deletions, and insertions assayed directly from PCR reactions eliminating the need for sample purification, shortening the hybridization time, and increasing the signal-to-noise ratio. Mixed samples containing up to a 20-fold excess of normal DNA and fragments up to 4 kb in size can been assayed. However, EMD scanning does not identify particular base changes that occur in mutation positive samples requiring additional sequencing procedures to identity of the mutation if necessary. CEL I enzyme can be used similarly to resolvase $T_4$ endonuclease VII as demonstrated in U.S. Pat. No. 5,869,245.

Another simple kit for detecting the EGFR mutations of the invention is a reverse hybridization test strip similar to Haemochromatosis StripAssay™(Viennalabs) for detection of multiple mutations in HFE, TFR2 and FPN1 genes causing Haemochromatosis. Such an assay is based on sequence specific hybridisation following amplification by PCR. For single mutation assays, a microplate-based detection system may be applied, whereas for multi-mutation assays, teststrips may be used as "macro-arrays". Kits may include ready-to use reagents for sample prep, amplification and mutation detection. Multiplex amplification protocols provide convenience and allow testing of samples with very limited volumes. Using the straightforward StripAssay format, testing for twenty and more mutations may be completed in less than five hours without costly equipment. DNA is isolated from a sample and the EGFR gene (or exons 18-21 or KDR or segments thereof) is amplified in vitro (e.g. PCR) and biotin-labelled, preferably in a single ("multiplex") amplification reaction. The PCR products are the selectively hybridized to oligonucleotide probes (wild-type and mutant specific) immobilized on a solid support such as a test strip in which the probes are immobilized as parallel lines or bands. Bound biotinylated amplicons are detected using szstreptavidin-alkaline phosphatase and color substrates. Such an assay can detect all or any subset of the mutations in table 1. With respect to a particular mutant probe band one of three signalling patterns are possible: (i) a band only for wild-type probe which indicates normal EGFR (ii) bands for both wild-type and a mutant probe which indicates heterozygous genotype and (iii) band only for the mutant probe which indicates homozygous mutant EGFR genotype. Accordingly there is further provides a method of detecting EGFR mutations of the invention comprising isolating nucleic acid from a sample, amplifying the EGFR gene, or fragment thereof (e.g. the KDR or exons 18-21 or smaller) such that the amplified nucleic acid comprises a ligand, contacting the amplified EGFR gene or fragment with a probe which comprises a detectable binding partner to the ligand and the probe is capable of specifically hydribizing to an EGFR mutation, and then detecting the hybridization of said probe to said amplified EGFR gene or fragment. In a particular embodiment the ligand is biotin and the binding partner is comprises avidin or streptavidin. In a particular embodiment the binding partner is steptavidin-alkaline which is detectable with color substrates. In a particular embodiment the probes are immobilized for example on a test strip wherein probes complementary to different mutations are separated from one another. Alternatively, the amplified nucleic acid is labelled with a radioisotope in which case the probe need not comprise a ligand.

The tumor samples were also analyzed for mutations in KRAS (as referred to as p21a). Particular mutations detected in exon 1 are: G12C; G12A; G12D; G12R; G12S; G12V; G13C; G13D which correlated with poor prognosis to chemotherapy as well as chemotherapy with erlotinib therapy. Accordingly, the invention further provides a method of identifying patients not responsive to therapy of an EGFR inhibitor such as erlotinib or erlotinib in combination with chemotherapy comprising determining the presence or absence of a KRAS mutation whereby the presence of said mutation indicates a patient will not respond to said therapy. Alternatively, there is provided a method for identifying a tumor in a human subject that is susceptible to treatment with an EGFR inhibitor comprising (i) determining the presence of a wild-type KRAS protein or gene in a sample of said tumor whereby the presence of a wild-type KRAS protein or gene indicates that the tumor is susceptible to treatment with an EGFR inhibitor or (ii) determining the presence of a mutated KRAS protein or gene in a sample of said tumor whereby the absence of a mutated KRAS protein or gene indicates that the tumor is susceptible to treatment with an EGFR inhibitor. In a particular embodiment the mutation is in exon I of K-Ras. In another embodiment the K-Ras mutation is at least one of G12C; G12A; G12D; G12R; G12S; G12V; G13C; G13D. Alternatively, individuals who have tumors which harbor mutant K-Ras may be treated with EGFR inhibitors when in concomitantly with a K-Ras inhibitor. Methods for determining the presence of K-Ras mutations are analogous to those used to identify EGFR mutations described in detail herein.

According to the diagnostic and prognostic method of the present invention, alteration of the wild-type EGFR gene is detected. Alterations of a wild-type gene according to the present invention encompasses all forms of mutations such as insertions, inversions, deletions, and/or point mutations. Somatic mutations are those which occur only in certain tissues, e.g., in the tumor tissue, and are not inherited in the germ line. Germ line mutations can be found in any of a body's tissues. If only a single allele is somatically mutated, an early neoplastic state is indicated. However, if both alleles are mutated then a late neoplastic state is indicated. The finding of EGFR mutations is therefore a diagnostic and prognostic indicator as described herein.

The EGFR mutations found in tumor tissues may result in increased signaling activity relative to wild-type EGFR leading to a cancerous state. In order to detect the alteration of the wild-type EGFR gene a sample or biopsy of the tumor is obtained by methods well known in the art and appropriate for the particular type and location of the tumor. For instance, samples of lung cancer lesions may be obtained by resection, bronchoscopy, fine needle aspiration, bronchial brushings, or from sputum, pleural fluid or blood. Means for enriching a tissue preparation for tumor cells are known in the art. For example, the tissue may be isolated from paraffin or cryostat sections. Cancer cells may also be separated from normal cells by flow cytometry or laser capture microdissection. These as well as other techniques for separating tumor from normal cells are well known in the art. If the tumor tissue is highly contaminated with normal cells, detection of mutations is more difficult.

Detection of point mutations may be accomplished by molecular cloning of the EGFR allele (or alleles) and sequencing that allele(s) using techniques well known in the art. Alternatively, the polymerase chain reaction (PCR) can be used to amplify gene sequences directly from a genomic DNA preparation from the tumor tissue. The DNA sequence of the amplified sequences can then be determined and mutations identified therefrom. The polymerase chain reaction is well known in the art and described in Saiki et al., Science 239:487, 1988; U.S. Pat. Nos. 4,683,203; and 4,683,195.

Specific primer pairs which can be used for PCR amplification of EGFR exons 18-21 include:

(SEQ ID NO: 39)
<5pEGFR.ex18.out> CAAATGAGCTGGCAAGTGCCGTGTC (SEQ ID NO: 40)
<3pEGFR.ex18.out> GAGTTTCCCAAACACTCAGTGAAAC

```
                                                             (SEQ ID NO: 41)
<5pEGFR.ex19.out>   GCAATATCAGCCTTAGGTGCGGCTC (SEQ ID NO: 42)
<3pEGFR.ex19.out>   CATAGAAAGTGAACATTTAGGATGTG (SEQ ID NO: 43)
<5pEGFR.ex20.out>   CCATGAGTACGTATTTTGAAACTC (SEQ ID NO: 44)
<3pEGFR.ex20.out>   CATATCCCCATGGCAAACTCTTGC (SEQ ID NO: 45)
<5pEGFR.ex21.out>   CTAACGTTCGCCAGCCATAAGTCC (SEQ ID NO: 46)
<3pEGFR.ex21.out>   GCTGCGAGCTCACCCAGAATGTCTGG (SEQ ID NO: 47)
<5pEGFR.ex18.in.m13f>  TGTAAAACGACGGCCAGTCAAGTGCCGTGTCCTGGCACCCAAGC (SEQ ID NO: 48)
<3pEGFR.ex18.in.m13r>  CAGGAAACAGCTATGACCCCAAACACTCAGTGAAACAAAGAG (SEQ ID NO: 49)
<5pEGFR.ex19.in.m13f>  TGTAAAACGACGGCCAGTCCTTAGGTGCGGCTCCACAGC (SEQ ID NO: 50)
<3pEGFR.ex19.in.m13r>  CAGGAAACAGCTATGACCCATTTAGGATGTGGAGATGAGC (SEQ ID NO: 51)
<5pEGFR.ex20.in.m13f>  TGTAAAACGACGGCCAGTGAAACTCAAGATCGCATTCATGC (SEQ ID NO: 52)
<3pEGFR.ex20.in.m13r>  CAGGAAACAGCTATGACCGCAAACTCTTGCTATCCCAGGAG (SEQ ID NO: 53)
<5pEGFR.ex21.in.m13f>  TGTAAAACGACGGCCAGTCAGCCATAAGTCCTCGACGTGG (SEQ ID NO: 54)
<3pEGFR.ex21.in.m13r>  CAGGAAACAGCTATGACCCATCCTCCCCTGCATGTGTTAAAC
```

Specific primer pairs which can be used for PCR amplification of K-Ras exon 1 include:

```
                                                             (SEQ ID NO: 55)
<5pKRAS-out>   TACTGGTGGAGTATTTGATAGTG (SEQ ID NO: 56)
<3pKRAS-out>   CTGTATCAAAGAATGGTCCTG (SEQ ID NO: 57)
<5pKRAS-in.m13f>  TGTAAAACGACGGCCAGTTAGTGTATTAACCTTATGTG (SEQ ID NO: 58)
<3pKRAS-in.m13r>  CAGGAAACAGCTATGACCACCTCTATTGTTGGATCATATTCG
```

The ligase chain reaction, which is known in the art, can also be used to amplify EGFR sequences. See Wu et al., Genomics, Vol. 4, pp. 560-569 (1989). In addition, a technique known as allele specific PCR can be used. (See Ruano and Kidd, Nucleic Acids Research, Vol. 17, p. 8392, 1989.) According to this technique, primers are used which hybridize at their 3'ends to a particular EGFR mutation. If the particular EGFR mutation is not present, an amplification product is not observed. Amplification Refractory Mutation System (ARMS) can also be used as disclosed in European Patent Application Publication No. 0332435 and in Newton et al., Nucleic Acids Research, Vol. 17, p.7, 1989. Insertions and deletions of genes can also be detected by cloning, sequencing and amplification. In addition, restriction fragment length polymorphism, (RFLP) probes for the gene or surrounding marker genes can be used to score alteration of an allele or an insertion in a polymorphic fragment. Single stranded conformation polymorphism (SSCP) analysis can also be used to detect base change variants of an allele. (Orita et al., Proc. Natl. Acad. Sci. USA Vol. 86, pp. 2766-2770, 1989, and Genomics, Vol. 5, pp. 874-879, 1989.) Other techniques for detecting insertions and deletions as are known in the art can be used.

Alteration of wild-type genes can also be detected on the basis of the alteration of a wild-type expression product of the gene. Such expression products include both the EGFR mRNA as well as the EGFR protein product. Point mutations may be detected by amplifying and sequencing the mRNA or via molecular cloning of cDNA made from the mRNA. The sequence of the cloned cDNA can be determined using DNA sequencing techniques which are well known in the art. The cDNA can also be sequenced via the polymerase chain reaction (PCR).

Mismatches, according to the present invention are hybridized nucleic acid duplexes which are not 100% complementary. The lack of total complementarity may be due to deletions, insertions, inversions, substitutions or frameshift mutations. Mismatch detection can be used to detect point mutations in the gene or its mRNA product. While these techniques are less sensitive than sequencing, they are simpler to perform on a large number of tumor samples. An example of a mismatch cleavage technique is the RNase protection method, which is described in detail in Winter et al., Proc. Natl. Acad. Sci. USA, Vol. 82, p. 7575, 1985 and Meyers et al., Science, Vol. 230, p. 1242, 1985. In the practice a the present invention the method involves the use of a labeled riboprobe which is complementary to the human wild-type EGFR gene coding sequence (or exons 18-21 or KDR thereof). The riboprobe and either mRNA or DNA isolated from the tumor tissue are annealed (hybridized) together and subsequently digested with the enzyme RNase A which is able to detect some mismatches in a duplex RNA structure. If a mismatch is detected by RNase A, it cleaves at the site of the mismatch. Thus, when the annealed RNA preparation is separated on an electrophoretic gel matrix, if a mismatch has been detected and cleaved by RNase A, an RNA product will be seen which is smaller than the full-length duplex RNA for the riboprobe and the mRNA or DNA. The riboprobe need not be the full length of the EGFR mRNA or gene but can be exons 18 through 21 or the EGFR KDR or segments thereof. If the riboprobe comprises only a segment of the EGFR mRNA or gene it will be desirable to use a number of these probes to screen the whole mRNA sequence for mismatches.

In a similar manner, DNA probes can be used to detect mismatches, through enzymatic or chemical cleavage. See, e.g., Cotton et al., Proc. Natl. Acad. Sci. USA, Vol. 85, 4397, 1988; and Shenk et al., Proc. Natl. Acad. Sci. USA, Vol. 72, p. 989, 1975. Alternatively, mismatches can be detected by shifts in the electrophoretic mobility of mismatched duplexes relative to matched duplexes. See, e.g., Cariello, Human Genetics, Vol. 42, p. 726, 1988. With either riboprobes or DNA probes, the cellular mRNA or DNA which might contain a mutation can be amplified using PCR before hybridization. Changes in DNA of the EGFR gene can also be detected using Southern hybridization, especially if the changes are gross rearrangements, such as deletions and insertions.

DNA sequences of the EGFR gene which have been amplified by use of polymerase chain reaction may also be screened using allele-specific probes. These probes are nucleic acid oligomers, each of which contains a region of the EGFR gene sequence harboring a known mutation. For example, one oligomer may be about 30 nucleotides in length, corresponding to a portion of the EGFR gene sequence. By use of a battery of such allele-specific probes, PCR amplification products can be screened to identify the presence of a previously identified mutation in the EGFR gene. Hybridization of allele-specific probes with amplified EGFR sequences can be performed, for example, on a nylon filter. Hybridization to a particular probe under stringent hybridization conditions indicates the presence of the same mutation in the tumor tissue as in the allele-specific probe.

Alteration of wild-type EGFR genes can also be detected by screening for alteration of wild-type EGFR protein. For example, monoclonal antibodies immunoreactive with EGFR can be used to screen a tissue. Lack of cognate antigen would indicate an EGFR mutation. Antibodies specific for products of mutant alleles could also be used to detect mutant EGFR gene product. Antibodies may be identified from phage display libraries. Such immunological assays can be done in any convenient format known in the art. These include Western blots, immunohistochemical assays and ELISA assays. Any means for detecting an altered EGFR protein can be used to detect alteration of wild-type EGFR genes.

Mutant EGFR genes or gene products can be detected from tumor or from other body samples such as urine, sputum or serum. The same techniques discussed above for detection of mutant EGFR genes or gene products in tumor samples can be applied to other body samples. Cancer cells are sloughed off from tumors and appear in such body samples. By screening such body samples, a simple early diagnosis can be achieved for many types of cancers. In addition, the progress of chemotherapy or radiotherapy can be monitored more easily by testing such body samples for mutant EGFR genes or gene products.

The methods of diagnosis of the present invention are applicable to any tumor in which EGFR has a role in tumorigenesis for example lung, breast, colon, glioma, bladder, liver, stomach and prostate. The diagnostic method of the present invention is useful for clinicians so that they can decide upon an appropriate course of treatment. For example, a tumor displaying alteration of both EGFR alleles might suggest a more aggressive therapeutic regimen than a tumor displaying alteration of only one EGFR allele.

The primer pairs of the present invention are useful for determination of the nucleotide sequence of a particular EGFR allele using the polymerase chain reaction. The pairs of single stranded DNA primers can be annealed to sequences within or surrounding the EGFR gene on in order to prime amplifying DNA synthesis of the EGFR gene itself. A set of these primers allows synthesis of all of the nucleotides of the EGFR exons 18 through 21. Allele specific primers can also be used. Such primers anneal only to particular EGFR mutant alleles, and thus will only amplify a product in the presence of the mutant allele as a template. In order to facilitate subsequent cloning of amplified sequences, primers may have restriction enzyme site sequences appended to their ends. Thus, all nucleotides of the primers are derived from EGFR exons 18-21 or sequences adjacent thereto except the few nucleotides necessary to form a restriction enzyme site. Such enzymes and sites are well known in the art. The primers themselves can be synthesized using techniques which are well known in the art. Generally, the primers can be made using oligonucleotide synthesizing machines which are commercially available. Design of particular primers is well within the skill of the art.

The nucleic acid probes provided by the present invention are useful for a number of purposes. They can be used in Southern hybridization to genomic DNA and in the RNase protection method for detecting point mutations already discussed above. The probes can be used to detect PCR amplification products. They may also be used to detect mismatches with the EGFR gene or mRNA using other techniques. Mismatches can be detected using either enzymes (e.g., SI nuclease), chemicals (e.g., hydroxylamine or osmium tetroxide and piperidine), or changes in electrophoretic mobility of mismatched hybrids as compared to totally matched hybrids. These techniques are known in the art. See Novack et al., Proc. Natl. Acad. Sci. USA, Vol. 83, p. 586, 1986. Generally, the probes are complementary to EGFR exon 18-21 sequences, although generally probes to the kinase domain and segments thereof are also contemplated. An entire battery of nucleic acid probes may be used to compose a kit for detecting alteration of wild-type EGFR genes. The kit allows for hybridization to the entire exon 18-21 sequence of the EGFR gene. The probes may overlap with each other or be contiguous.

If a riboprobe is used to detect mismatches with mRNA, it is complementary to the mRNA of the EGFR gene. The riboprobe thus is an antisense probe in that it does not code for the EGFR protein because it is complementary to the sense strand. The riboprobe generally will be labeled with a radioactive, calorimetric, or fluorometric material, which can be accomplished by any means known in the art. If the riboprobe is used to detect mismatches with DNA it can be of either polarity, sense or anti-sense. Similarly, DNA probes also may be used to detect mismatches.

Predisposition to cancers can be ascertained by testing any tissue of a human for mutations of the EGFR gene. For example, a person who has inherited a germ line EGFR mutation would be prone to develop cancers. This can be determined by testing DNA from any tissue of the body. For example, blood can be drawn and DNA extracted from the cells of the blood. In addition, prenatal diagnosis can be accomplished by testing fetal cells, placental cells, or amniotic fluid for mutations of the EGFR gene. Alteration of a wild-type EGFR allele, whether for example, by point mutation or by deletion, can be detected by any of the means discussed above.

EXAMPLES

Example 1

Slide Preparation—Deparaffinization and Staining

Submersed sections in the following solutions:
1. Fresh xylenes (to depariffinize the sections)—5 min
2. Fresh xylenes—5 min
3. 100% ethanol—15 sec
4. 95% ethanol—15 sec
5. 70% ethanol—15 sec
6. Deionized water—15 sec
7. Mayer's Hematoxylin—30 sec
8. Deionized water—rinse (×2)—15 sec
9. 70% ethanol—15 sec
10. Eosin Y—5 sec
11. 95% ethanol—15 sec
12. 95% ethanol—15 sec
13. 100% ethanol—15 sec
14. 100% ethanol—15 sec
15. Xylenes (to ensure dehydration of the section)—60 sec
16. Air-dried for approximately 2 minutes or gently used air gun to completely remove xylenes.
17. The tissue was then ready for LCM.

Example 2

Laser Capture Microdissection and DNA Extraction

Materials:
PixCell II LCM System
CapSure HS or CapSure Macro LCM caps
ExtractSure device (HS only)
Razor blades (factory sterile)
0.5 ml tubes
0.2 ml tubes
PicoPure DNA extraction Kit
65° C. incubator
Procedure:
1. Placed CapSure cap over area of tissue to be collected
2. Lased over desired area
3. Lifted cap off tissue.
4. Dispensed 20 ul of PicoPure digest buffer with Proteinase K into 0.5ml tube.
5. Placed cap with dissected material into tube to form a tight seal.
6. Inverted tube such that digest buffer covered cap.
7. Incubated at 65° C. for 24 hours.
8. Spun tube with cap to collect digested material in the bottom of the tube.
9. Transferred digest to 0.2 ml strip tube.
10. Inactivated Proteinase K at 95° C. for 10 minutes in a thermocycler with a heated lid.
11. Used 1-2 ul of sample in a 50 ul PCR reaction. No clean-up was necessary.

Example 3

PCR Amplification

PCR Primers:
Primer pairs were designed for each exon to be sequenced (EGFR exons 18, 19, 20 and 21). Primer sequences used were as follows:

```
                                                            (SEQ ID NO: 39)
<5pEGFR.ex18.out>  CAAATGAGCTGGCAAGTGCCGTGTC (SEQ ID NO: 40)
<3pEGFR.ex18.out>  GAGTTTCCCAAACACTCAGTGAAAC (SEQ ID NO: 41)
<5pEGFR.ex19.out>  GCAATATCAGCCTTAGGTGCGGCTC (SEQ ID NO: 42)
<3pEGFR.ex19.out>  CATAGAAAGTGAACATTTAGGATGTG (SEQ ID NO: 43)
<5pEGFR.ex20.out>  CCATGAGTACGTATTTTGAAACTC (SEQ ID NO: 44)
<3pEGFR.ex20.out>  CATATCCCCATGGCAAACTCTTGC (SEQ ID NO: 45)
<5pEGFR.ex21.out>  CTAACGTTCGCCAGCCATAAGTCC (SEQ ID NO: 46)
<3pEGFR.ex21.out>  GCTGCGAGCTCACCCAGAATGTCTGG
```

-continued

```
                                                           (SEQ ID NO: 47)
<5pEGFR.ex18.in.m13f>  TGTAAAACGACGGCCAGTCAAGTGCCGTGTCCTGGCACCCAAGC (SEQ ID NO: 48)
<3pEGFR.ex18.in.m13r>  CAGGAAACAGCTATGACCCCAAACACTCAGTGAAACAAAGAG (SEQ ID NO: 49)
<5pEGFR.ex19.in.m13f>  TGTAAAACGACGGCCAGTCCTTAGGTGCGGCTCCACAGC (SEQ ID NO: 50)
<3pEGFR.ex19.in.m13r>  CAGGAAACAGCTATGACCCATTTAGGATGTGGAGATGAGC (SEQ ID NO: 51)
<5pEGFR.ex20.in.m13f>  TGTAAAACGACGGCCAGTGAAACTCAAGATCGCATTCATGC (SEQ ID NO: 52)
<3pEGFR.ex20.in.m13r>  CAGGAAACAGCTATGACCGCAAACTCTTGCTATCCCAGGAG (SEQ ID NO: 53)
<5pEGFR.ex21.in.m13f>  TGTAAAACGACGGCCAGTCAGCCATAAGTCCTCGACGTGG (SEQ ID NO: 54)
<3pEGFR.ex21.in.m13r>  CAGGAAACAGCTATGACCCATCCTCCCCTGCATGTGTTAAAC

K-Ras oligos for PCR
                                                           (SEQ ID NO: 55)
<5pKRAS-out>  TACTGGTGGAGTATTTGATAGTG (SEQ ID NO: 56)
<3pKRAS-out>  CTGTATCAAAGAATGGTCCTG (SEQ ID NO: 57)
<5pKRAS-in.m13f>  TGTAAAACGACGGCCAGTTAGTGTATTAACCTTATGTG (SEQ ID NO: 58)
<3pKRAS-in.m13r>  CAGGAAACAGCTATGACCACCTCTATTGTTGGATCATATTCG
```

Nested amplification of the primary PCR product was performed using intron-specific primer pairs located within the primary PCR product. These nested primers pairs were tagged with M13f and M13rev sequences.

First Round of PCR:
PCR Reaction:

| | |
|---|---|
| DNA | 0.5 to 30 ng |
| Primers | 250 nM/each outer primers |
| dNTPs | 0.2 mM each (Roche cat#1581295) |
| MgCl$_2$ | 1.5 mM (15 mM 10 × buffer) |
| Enzyme | 1.5 U/RX Expand High fidelity Taq (Roche cat#1759078) |
| | 50 ul reaction volume |

Thermocycler Conditions:
95° C.-3 minutes
94° C -30 seconds repeat 35 times
58° C.-30 seconds
72° C.-1 minute
72° C.-8 minutes
4° C.-forever Second Round of PCR:
PCR Reaction:

| | |
|---|---|
| DNA | 1 ul from first round PCR reaction |
| Primers | 250 nM/each inner primers |
| dNTPs | 0.2 mM each (Roche cat#1581295) |
| MgCl$_2$ | 1.5 mM (15 mM 10 × buffer) |
| Enzyme | 1.5 U/RX Expand High fidelity Taq (Roche cat#1759078) |
| | 50 ul reaction volume |

Thermocycler Conditions:
95° C.-3 minutes
94° C -30 seconds repeat 30 times
58° C.-30 seconds
72° C -1 minute
72° C.-8 minutes
4° C.-forever Isolation of PCR Products:

PCR reaction products were run on E-Gel 2% agarose gels (Invitrogen, cat# G6018-02) for quality control. PCR products were purified directly using the Qiaquick 96 PCR purification kit (Qiagen, cat#28181) or gel purified as was necessary. For gel purification, the PCR product was excised from the E-gel and the DNA purified using Qiaquick 96 PCR purification kit with a gel extraction protocol.(Qiagen, cat#28181).

Example 4

Sequencing

Nested sequencing primers or standard M13f and M13rev sequencing primers for tagged PCR products were used to sequence the purified PCR products. Sequences were as follows:

```
<m13f>  TGTAAAACGACGGCCAGT    (SEQ ID NO: 59)

<m13r>  CAGGAAACAGCTATGACC    (SEQ ID NO: 60)
```

Purified PCR products were diltuted and cycle-sequenced using the BigDye Terminator Kit (ABI, Foster City, Calif.) according to manufacturer's instructions.

Reaction Mix:
  5 ul DNA (25-100 ng PCR product)
  6 ul water
  1 ul primer diluted to 0.25 OD/100 ul with water (m13f or m13r or sequence specific primer)
  2 ul BigDye v3.1
  6 ul Dilution Buffer (equivalent of ABI 5× Dilution Buffer)
Cycle Sequencing:
  Conditions:
  96° C.-2.5 minutes—initial denaturation
  96° C.-10 seconds
  50° C.-5 seconds
  60° C.-4 minutes
  repeated for 25 to 50 total cycles
Reaction Cleanup:
  Removed unincorporated nucleotides using:
  8% sephadex
  500 ul in Edge BioSystem 96-well block
  spin@ 750g for 2 minutes
Analysis:
  Reaction products were electrophoresed on ABI3700 or ABI3730 sequencing instruments. Electropherograms were analyzed for mutations using commercially available analysis programs, such as Sequencher (Gene Codes, Corp), and with custom tools.

Example 5

Dose Response

Human epidermal growth factor receptor (EGFR) wild-type and mutant constructs used in this study were epitope-tagged at the N-terminus with the herpes simplex virus signal sequence of gD, replacing the endogenous EGFR signal sequence (Schaefer et al. 1999 J. Biol. Chem. 274, 859-866). Cos7 cells were seeded in 12 well dishes in normal growth medium 24 hours prior to transfection. Cells were transfected with 0.25 ug per well with expression plasmid DNAs (pRK5.gD.EGFR wild-type, pRK5.gD.EGFR. L858R, or pRK5.gD.EGFR.del(E746-S752)) using LipofectAMINE 2000 following manufacturer's recommended protocol (Invitrogen). Twenty-four hours post-transfection, cells were serum starved for six hours in serum free DMEM. One hour prior to stimulation, transfected cells were preincubated with the indicated concentrations of erlotinib. Transfected cells were stimulated with 1 nM TGFα for 10 minutes. Cells were lysed directly in the wells using reducing Laemmli buffer. Receptor autophosphorylation, an index of EGFR receptor activation by growth factor stimulation, was detected by Western blotting using an HRP-conjugated anti-phosphotyrosine antibody (Oncogene Sciences, AB-4). Transfection efficiency was evaluated using an antibody specific for the gD epitope tag (5B6). Level of receptor activation was evaluated from the autoradiograms using NIH Image software. These data were then used to generate a graph from which an IC50 was calculated using a 4 parameter fit function. As illustrated by the results below, erlotinib has a greater affinity to EGFR containing mutations compared to wild-type EGFR.

| EGFR construct | inhibition (IC50) |
| --- | --- |
| WT EGFR-gD | 50 nM |
| L858R EGFR-gD | 20 nM |
| del(746-752) EGFR-gD | 5 nM |

I claim:

1. A method for determining whether a colorectal tumor in a human subject is responsive to treatment with cetuximab or panitumumab, comprising (i) assaying for the presence of a wild-type KRAS gene encoding a glycine residue at codon 12 and 13 in a sample of said tumor or for the presence of a mutated KRAS gene in a sample of said tumor, wherein said mutated KRAS gene encodes a G12C; G12A; G12D; G12R; G12S; G12V; or G13C mutation and (ii) identifying the tumor in the human subject as responsive to treatment with cetuximab or panitumumab when the wild-type KRAS gene is present, or identifying the tumor in a human subject as not responsive to treatment with cetuximab or panitumumab when said mutated KRAS gene is present.

2. A method for determining whether a colorectal tumor in a human subject is not responsive to therapy with cetuximab or panitumumab, comprising:

assaying for the presence of a KRAS gene having a mutation in a sample of said tumor, wherein said KRAS gene encodes a G12C; G12A; G12D; G12R; G12S; G12V; or G13C mutation and identifying the presence of the KRAS gene mutation indicates that the tumor is not responsive to treatment with cetuximab or panitumumab.

3. A method for identifying a colorectal tumor in a human subject that is responsive to treatment with cetuximab or panitumumab comprising (i) assaying for the presence of a wild-type KRAS gene encoding a glycine residue at codon 12 and 13 in a sample of said tumor or for the presence of a mutated KRAS gene in a sample of said tumor, wherein said mutated KRAS gene encodes a G12C; G12A; G12D); G12R; G12S; G12V; or G13C mutation and (ii) identifying the tumor in the human subject as responsive to treatment with cetuximab or panitumumab when the wild-type KRAS gene is present, or identifying the tumor in a human subject as not responsive to treatment with cetuximab or panitumumab when said mutated KRAS gene is present.

4. A method for determining whether a colorectal tumor in a human subject is responsive to treatment with panitumumab, comprising (i) assaying for the presence of a wild-type KRAS gene encoding a glycine residue at codon 12 and 13 in a sample of said tumor or for the presence of a mutated KRAS gene in a sample of said tumor, wherein said mutated KRAS gene encodes a G12C; G12A; G12D; G12R; G12S; G12V; or G13C mutation and (ii) identifying the tumor in a human subject as responsive to treatment with panitumumab when the wild-type KRAS gene is present or identifying the tumor in the human subject as not responsive to treatment with panitumumab when said mutated KRAS gene is present.

5. A method for determining whether a colorectal tumor in a human subject is responsive to treatment with cetuximab, comprising (i) assaying for the presence of a wild-type KRAS gene encoding a glycine residue at codon 12 and 13 in a sample of said tumor or for the presence of a mutated KRAS gene in a sample of said tumor, wherein said mutated KRAS gene encodes a G12C; G12A; G12D; G12R; G12S; G12V; or G13C mutation and (ii) identifying the tumor in the human subject as responsive to treatment with cetuximab when the wild-type KRAS is present or identifying the tumor in a human subject as not responsive to treatment with cetuximab when the mutated KRAS is present.

6. The method of claim 1, 2, 3, 4, or 5 wherein said KRAS gene mutation encodes a G12C mutation.

7. The method of claim 6 wherein the G12C mutation is detected using an amplification assay, a hybridization assay or by molecular cloning and sequencing.

8. The method of claim 1, 2, 3, 4, or 5 wherein said KRAS gene mutation encodes a G12A mutation.

9. The method of claim 8 wherein the G12A mutation is detected using an amplification assay, a hybridization assay or by molecular cloning and sequencing.

10. The method of claim 1, 2, 3, 4, or 5 wherein said KRAS gene mutation encodes a G12D mutation.

11. The method of claim 10 wherein the G12D mutation is detected using an amplification assay, a hybridization assay or by molecular cloning and sequencing.

12. The method of claim 1,2,3,4, or 5 wherein said KRAS gene mutation encodes a G12R mutation.

13. The method of claim 12 wherein the G12R mutation is detected using an amplification assay, a hybridization assay or by molecular cloning and sequencing.

14. The method of claim 1,2,3,4, or 5 wherein said KRAS gene mutation encodes a G12S mutation.

15. The method of claim 14 wherein the G12S mutation is detected using an amplification assay, a hybridization assay or by molecular cloning and sequencing.

16. The method of claim 1,2,3,4, or 5 wherein said KRAS gene mutation encodes a G12V mutation.

17. The method of claim 16 wherein the G12V mutation is detected using an amplification assay, a hybridization assay or by molecular cloning and sequencing.

18. The method of claim 1,2,3,4, or 5 wherein said KRAS gene mutation encodes a G13C mutation.

19. The method of claim 18 wherein the G13C mutation is detected using an amplification assay, a hybridization assay or by molecular cloning and sequencing.

20. The method of claim 1,2,3,4, or 5 in which the KRAS gene in the tumor sample is detected using a DNA amplification assay.

21. The method of claim 13 in which a polymerase chain reaction is used to amplify the KRAS gene in the tumor sample.

22. The method of claim 13 in which a ligase chain reaction is used to amplify the KRAS gene in the tumor sample.

23. The method of claim 1,2,3,4, or 5 in which a DNA hydridization assay is used to detect the KRAS gene in the tumor sample.

24. The method of claim 1,2,3,4, or 5 in which the KRAS gene in the tumor sample is molecularly cloned and sequenced.

* * * * *